(12) United States Patent
Lee et al.

(10) Patent No.: US 10,441,686 B2
(45) Date of Patent: Oct. 15, 2019

(54) STENT HAVING FUNCTIONAL MATERIAL COATED ON CELL SPACE THEREOF

(71) Applicants: UTAH-INHA DDS & ADVANCED THERAPEUTICS RESEARCH CENTER, Incheon (KR); NEXTBIOMEDICAL CO., LTD., Incheon (KR)

(72) Inventors: Don Haeng Lee, Seoul (KR); Jong Chae Park, Sejong-si (KR); Dong Gon Kim, Incheon (KR); Choong Ryeol Choi, Incheon (KR)

(73) Assignees: UTAH-INHA DDS & ADVANCED THERAPEUTICS RESEARCH CENTER, Incheon (KR); NEXTBIOMEDICAL CO., LTD., Incheon (KR)

( * ) Notice: Subject to any disclaimer, the term of this patent is extended or adjusted under 35 U.S.C. 154(b) by 127 days.

(21) Appl. No.: 15/545,058

(22) PCT Filed: Mar. 9, 2016

(86) PCT No.: PCT/KR2016/002352
§ 371 (c)(1),
(2) Date: Jul. 20, 2017

(87) PCT Pub. No.: WO2016/144096
PCT Pub. Date: Sep. 15, 2016

(65) Prior Publication Data
US 2018/0008752 A1   Jan. 11, 2018

(30) Foreign Application Priority Data

Mar. 12, 2015 (KR) ........................ 10-2015-0034550

(51) Int. Cl.
| | | |
|---|---|---|
| *A61L 31/08* | (2006.01) | |
| *A61L 31/02* | (2006.01) | |
| *A61L 31/10* | (2006.01) | |
| *A61L 31/14* | (2006.01) | |
| *A61L 31/16* | (2006.01) | |
| *A61L 31/18* | (2006.01) | |

(52) U.S. Cl.
CPC ............ *A61L 31/08* (2013.01); *A61L 31/022* (2013.01); *A61L 31/10* (2013.01); *A61L 31/148* (2013.01); *A61L 31/16* (2013.01); *A61L 31/18* (2013.01); *A61L 2300/416* (2013.01)

(58) Field of Classification Search
CPC ........ A61L 31/08; A61L 31/18; A61L 31/022; A61L 31/148; A61L 31/10; A61L 31/16; A61L 2300/416; A61F 2/04
See application file for complete search history.

(56) References Cited

U.S. PATENT DOCUMENTS

| | | | |
|---|---|---|---|
| 6,764,709 B2 * | 7/2004 | Flanagan ............... | B05D 3/065 427/2.1 |
| 2005/0245637 A1 | 11/2005 | Hossainy et al. ............. | 523/113 |
| 2006/0217799 A1 | 9/2006 | Mailander et al. | |
| 2008/0300673 A1 | 12/2008 | Clerc et al. | |
| 2010/0262230 A1 | 10/2010 | Vecerina et al. ............. | 623/1.46 |
| 2012/0078348 A1 | 3/2012 | Orr | |
| 2012/0303112 A1 | 11/2012 | Armstrong et al. ......... | 623/1.16 |
| 2016/0128849 A1 | 5/2016 | Yan et al. ................. | A61F 2/82 |

FOREIGN PATENT DOCUMENTS

| | | | | |
|---|---|---|---|---|
| JP | 2008-539245 | | 11/2008 | ............... A61K 9/52 |
| JP | 2009-505732 A | | 2/2009 | |
| JP | 5312018 | | 10/2013 | |
| KR | 10-2010-0123818 | | 11/2010 | ............. B05B 13/04 |
| KR | 10-2012-0117169 | | 10/2012 | ............... A61F 2/82 |
| KR | 10-2012-0131250 | | 12/2012 | ............... A61F 2/82 |
| KR | 10-2014-0004171 | | 1/2014 | ............... A61F 2/82 |
| WO | WO-2013/025535 A1 | | 2/2013 | |
| WO | WO-2015/021402 A1 | | 2/2015 | |

OTHER PUBLICATIONS

Japanese Office Action from corresponding Japanese Patent Application No. 2017-552775, dated May 1, 2018, and it's English translation.
Extended European Search Report from corresponding European Patent Application No. 16761983.2, dated Sep. 12, 2018.
International Search Report from corresponding PCT Application No. PCT/KR2016/002352 dated Jun. 14, 2016 and its English translation.
Office Action from corresponding Korean Patent Application No. 10-2016-0028399 dated May 15, 2017 and its English translation.

* cited by examiner

*Primary Examiner* — Robert S Cabral
(74) *Attorney, Agent, or Firm* — Harness, Dickey & Pierce, P.L.C.

(57) ABSTRACT

The present invention relates to a stent having a functional material coated on a cell space (safe coating space) thereof. The stent of the present invention, as a stent having a space for mounting and coating drugs and other materials for expanding the functions of the stent, is highly feasible as an actual product in consideration of the structure, transfer device, and manufacturing process of the stent as a whole, and secures a coating space (safe coating space) of a functional material in a cell of the stent through quantitative and qualitative modelling. Since an additional increase in volume does not occur even when the stent is press-mounted in a transfer device as a result of mounting a radio marker or a drug in the coating space, the stent of the present invention has excellent radio opacity without obstructing the loading and deployment of the stent, and may stably mount a great amount of a functional drug.

17 Claims, 35 Drawing Sheets a) Coating form at hook region  b) Coating form at cross region a) Before Compression    b) After Compression $$R_{tb} = \frac{W_{avg}}{2\tan(180/N_x)}$$

$$N_x = \frac{180}{\tan^{-1}(W_{avg}/(2R_{tb}))}$$

$$R_{tb} = R_{ib} + H_{hook}$$

though the functional coating of only about 10 μm
STENT HAVING FUNCTIONAL MATERIAL COATED ON CELL SPACE THEREOF

CROSS-REFERENCE TO RELATED APPLICATIONS

This application is a national phase application of PCT Application No. PCT/KR2016/002352, filed on 9 Mar. 2017, which claims the benefit and priority to Korean Patent Application No. 10-2015-0034550, filed 12 Mar. 2015. The entire disclosures of the applications identified in this paragraph are incorporated herein by references.

TECHNICAL FIELD

The present invention relates to a stent having a cell area (secure coating area) coated with a functional coating material.

BACKGROUND ART

The conventional stent functional coating method has proposed the formation of a dual-layer structure and a multi-layer structure through coating, as shown in FIG. 1. However, a stent with a large diameter needs to be compressed into a small-diameter stent and loaded on a thin catheter, called a delivery device, to move to a target site in the body to be treated, and also, in the target site, the stent loaded in the catheter needs to be safely withdrawn from the catheter and then expanded. Therefore, in the preparation step, the stent needs to be smoothly inserted into thin catheter and, also in the procedure step for a patient, the stent needs to be smoothly withdrawn from the catheter, so that the procedure can be successfully completed.

If a smooth withdrawal is not ensured in the procedure step, both an operator and a patient will face a difficult situation.

Therefore, in order to ensure a smooth insertion and withdrawal of the stent, even after the stent is functionally coated and then compressed for the insertion into the thin catheter, the stent should maintain its basic secure volume without an additional stent volume increase causing interference.

For example, a biliary stent with a diameter of 10 mm and a length of 100 mm woven in a hook shape using 0.12-mm diameter Ni—Ti wire, which is a shape-memory alloy, is coated with a single layer of silicon of about 30 μm, and when such a stent is inserted into, and withdrawn (deployed) from, a catheter with an outer diameter of 8 fr (2.64 mm), a force of about 15-20 N is required (further increased due to problems, such as flexion, after the insertion into the body).

However, when a functional coating of only about 10 μm is further applied to the stent, it is almost impossible to compress the stent and load the stent in the thin catheter in the preparation step. Even if the stent is forcibly loaded, the withdrawal (deployment) of the stent is difficult during the procedure, and thus, both the operator and the patient face a difficult situation, such as the delivery device being broken.

The multilayer coating method, wherein coating layers with approximately 5-10 μm per layer are formed in order to give particular functionality, is difficult to apply in an existing stent system, and rather, it is reasonable to develop and apply a novel stent system.

Therefore, in order to apply a particular functional coating to an existing stent system, a technical approach different from the conventional method is needed.

First, a structure of a stent with hooks and crosses formed by weaving a wire material is shown in FIG. 2.

When the stent in a state of FIG. 2 is subjected to a general external coating, a coating form, in which the outer periphery of the wire is very thinly coated and the portions in contact with inner cells are thickly coated, is observed as shown in FIG. 3. For further understanding, a coating form of a section of one wire is shown in FIG. 4.

In this state, if a coating for a dual-layer or multi-layer structure is conducted for an additional functional coating, the coating is implemented on the already formed coating layer as shown in FIG. 5, and thus, the top side of the wire is coated thicker than before and the lateral side of the wire is also coated thickly, making it difficult for the stent to be substantially compressed and loaded in the delivery device.

Even if an existing coating layer is partially coated the repair of a coated portion in the actual stent preparation site, the same problem occurs, causing difficulty in the preparation process in which the stent is loaded in the delivery device.

An ordinary single-layer coating process is controlled such that the coated stent has such a coating thickness as to be compressed and inserted (loaded) in the delivery device.

Since there is a basic coating thickness required to impart specific functionality, the arbitrary reduction of the coating thickness only for the loading convenience in the delivery device may cause secondary clinical problems after the stent has been applied to the patient.

For example, in a single-layer coating applied to a non-vascular stent, a membrane is formed through the coating of silicon or the like in order to mainly prevent the ingrowth of cancer tissues into the stent, and here, the coating thickness is approximately 30 μm.

Here, if the thickness of the coating is reduced to facilitate the insertion of the stent to be loaded in the delivery device (in the catheter), there may be damages, such as tearing of the coated membrane, when the stent is loaded. If the damaged stent is applied to the patient, a coating membrane cannot achieve the intended purpose, resulting in the ingrowth of cancer tissues into the stent, causing a deterioration in mechanical strength of the coating membrane, thus increasing the possibility that the coating membrane is damaged early.

Therefore, in order to proceed with an additional functional coating without degrading the basic performance of the coating layer after the single layer is coated, the in-depth analysis of the structural shape of the stent and the behavior (reactivity) thereof by external force, such as compression, is conducted, and then an additional functional coating area (secure coating area) that will not affect the loading (insertion) and deployment (withdrawal) of the stent is found (ensured), and then a coating process needs to be performed on the basis of the corresponding area.

For this purpose, it is necessary to design a secure coating area by modeling hooks and crosses of the stent and schematizing the state where the hook and the cross areas are compressed and loaded in the delivery device.

That is, the present inventors have recognized the need for a technology capable of ensuring an area for a functional coating without increasing the deployment force required for the loading and withdrawal of the stent, intensively considering a structure of a stent, an insertion tool, and a preparation process, for a functional coating implement technology applicable to an existing stent system other than the multi-layer coating method.

Throughout the entire specification, many papers and patent documents are referenced and their citations are represented. The disclosure of the cited papers and patent documents are entirely incorporated by reference into the present specification, and the level of the technical field within which the present invention falls and the details of the present invention are explained more clearly.

RELATED ART DOCUMENT

Patent Document

Korean Patent Publication No. 10-2012-0082086

DETAILED DESCRIPTION OF THE INVENTION

Technical Problem

The present inventors have studied a method for ensuring coating areas for loading drugs and other materials to expand the functions of a stent having a high possibility of realization as an actual product, intensively considering the structure of a stent, a delivery device, and the preparation process. As a result, as described later, the present inventors have ensured a coating area (secure coating area) for a functional material in a cell area of the stent through qualitative and quantitative modeling, and the present inventors have verified that, as a result of loading a radiation marker or a drug in such a coating area, the stent had no additional volume increase even when compressed and loaded in the delivery device, leading to a more excellent radiopaque effect than existing ones, without the interference of the loading and deployment of the stent, and the present inventors have also verified through drug release profiles that a large amount of functional drugs can be securely loaded.

Therefore, a purpose of the present invention is to provide a stent having a cell area (secure coating area) coated with a functional material.

Other purposes and advantages of the present invention will become more obvious with the following detailed description of the invention, claims, and drawings.

Technical Solution

In an aspect of the present invention, the present disclosure provides a stent having a cell area coated with a functional material.

According to an embodiment of the present invention, the cell area has a volume defined by equation 1 below:

$$V_{sa} = A_{sa} \times I_{scx} \quad \text{Equation 1}$$

wherein in equation 1, $V_{sa}$ represents the average secure coating volume per node and $A_{sa}$ represents the average secure coating area per node, the node meaning a hook or cross; and $I_{scx}$ represents the secure axial length of cell.

Preferably, the stent is a wire stent having a cell area including a hook, a cross, or a hook and a cross.

The secure axial length of cell ($I_{scx}$) is defined by equation 2:

$$I_{scx} = \quad \text{Equation 2}$$

-continued $$\begin{cases} I_{cx}/(1-r_{short}) - L_{hook}: & I_{scx} \text{ is between hook and hook} \\ I_{cx}/(1-r_{short}) - (L_{hook} + L_{cross})/2: & I_{scx} \text{ is between hook and cross} \\ I_{cx}/(1-r_{short}) - L_{cross}: & I_{scx} \text{ is between cross and cross} \end{cases}$$

wherein in equation 2, $I_{cx}$ represents the axial length of cell, $r_{short}$ represents the shortening ratio and is defined by equation 3 below, $L_{hook}$ represents the nominal length of hook node and is defined by equation 4 below, and $L_{cross}$ represents the nominal length of hook node and is defined by equation 5 below; wherein in equation 3 below, $L_{stent.load}$ represents the length of stent when the stent is loaded in a delivery device, $L_{stent}$ represents the length of stent before the stent is loaded in the delivery device, and the $r_{short}$ has a value of 0.2-0.6; wherein in equations 4 and 5 below, $\phi_w$ represents the diameter of a wire; wherein in equation 4 below, $SF_{lh}$ represents the length scale factor of hook node and has a value of 4; and wherein in equation 5 below, $SF_{lc}$ represents the length scale factor of cross node and has a value of 5.

$$r_{short} = (L_{stent.load} - L_{stent})/L_{stent.load} \quad \text{Equation 3}$$

$$L_{hook} = \phi_w \times SF_{lh} \quad \text{Equation 4}$$

$$L_{cross} = \phi_w \times SF_{lc} \quad \text{Equation 5}$$

The average secure coating area per node ($A_{sa}$) is defined by equation 6 below; and wherein in equation 6, $A_{sx}$ represents the maximum secure coating area and is defined by equation 7 below, and $N_t$ represents the total number of nodes per section of stent and is defined by equation 8 below:

$$A_{sa} = A_{sx}/N_t \quad \text{Equation 6}$$

$$A_{sx} = \pi(R^2_{ob} - R^2_{ib}) - A_{nd} \quad \text{Equation 7}$$

$$N_t = N_h + N_c \quad \text{Equation 8}$$

wherein in equation 7 above, $R_{ob}$ represents the radius of outmost boundary, $R_{ib}$ represents the radius of inmost boundary, and $A_{nd}$ represents the node area per section of stent; and wherein in equation 8 above, $N_h$ represents the number of hook nodes per section of stent, and $N_c$ represents the number of cross nodes per section of stent.

The radius of outmost boundary ($R_{ob}$) is defined by equation 9; the radius of inmost boundary ($R_{ib}$) is defined by equation 10; and $A_{nd}$ is defined by equation 11:

$$R_{ob} = \frac{R_{tb}}{\cos(180/N_x)} \quad \text{Equation 9}$$

$$R_{ib} = \frac{W_{avg}}{2 \cdot \tan(180/N_t)} \quad \text{Equation 10}$$

$$A_{nd} = (W_{hook} \times H_{hook} \times N_h) + (W_{cross} \times H_{cross} \times N_c) \quad \text{Equation 11}$$

wherein in equation 9 above, $R_{tb}$ represents the inradius of outmost boundary, and $N_x$ represents the number of virtual hook nodes tangential on the outmost boundary; wherein in equation 10 above, $W_{avg}$ represents the average nominal width of node per section of stent, equation 10 above satisfying conditions of $\pi(N_t \tan(180/N_t)) \leq 1$; and wherein in equation 11 above, $W_{hook}$ represents the nominal width of hook node, $H_{hook}$ represents the nominal height of hook node, $W_{cross}$ represents the nominal width of cross node, and $H_{cross}$ represents the nominal height of cross node.

The average nominal width of node per section of stent ($W_{avg}$) is defined by equation 12 below; the number of virtual hook nodes tangential on the outmost boundary ($N_x$) is defined by equation 13 below; the nominal height of hook node ($H_{hook}$) is defined by equation 14 below; and the nominal height of cross node ($H_{cross}$) is defined by equation 15 below:

$$W_{avg} = W_{total}/N_t \qquad \text{Equation 12}$$

$$N_x = \left\| \frac{180}{\tan^{-1}(W_{avg}/(2R_{tb}))} \right\| \qquad \text{Equation 13}$$

$$H_{hook} = \phi_w \times SF_{hh} \qquad \text{Equation 14}$$

$$H_{cross} = \phi_w \times SF_{hc} \qquad \text{Equation 15}$$

wherein in equation 12 above, $W_{total}$ represents the sum total of nominal width of all nodes per section of stent; wherein in equation 13 above, $R_{tb}$ represents the inradius of outmost boundary; wherein in equations 14 and 15 above, $\phi_w$ represents the diameter of wire; wherein in equation 14 above, $SF_{hh}$ represents the height scale factor of hook node and has a value of 3; and wherein in equation 15 above, $SF_{hc}$ represents the length scale factor of cross node and has a value of 2.

The sum total of nominal width of all nodes per section of stent ($W_{total}$) is defined by equation 16 below; and the inradius of outmost boundary ($R_{tb}$) is defined by equation 17 below:

$$W_{total}=(W_{hook} \times N_h + W_{cross} \times N_c) \qquad \text{Equation 16}$$

$$R_{tb}=R_{ib}+H_{hook} \qquad \text{Equation 17}$$

wherein in equation 16 above, $W_{hook}$ represents the nominal width of hook node, and $W_{cross}$ represents the nominal width of cross node.

The stent nominal width of hook node ($W_{hook}$) is defined by equation 18 below; and the nominal width of cross node ($W_{cross}$) is defined by equation 19 below:

$$W_{hook}=\phi_w \times SF_{wh} \qquad \text{Equation 18}$$

$$W_{cross}=\phi_w \times SF_{wc} \qquad \text{Equation 19}$$

wherein in equations 18 and 19 above, $\phi_w$ represents the diameter of wire; wherein in equation 18 above, $SF_{wh}$ represents the width scale factor of hook node and has a value of 3.3; and wherein in equation 19 above, $SF_{wc}$ represents the width scale factor of cross node and has a value of 2.

According to another embodiment of the present invention, the cell area has a volume defined by equation 20 below:

$$V=2R \times (I_{cx}-2R) \times h \qquad \text{Equation 20}$$

wherein in equation 20 above, R represents the radius of cell axial end, $I_{cx}$ represents the axial length of cell, and h represents the thickness or height of cell.

Preferably, the stent is a tube stent having a cell area formed by a strut.

According to another embodiment of the present invention, the functional material may include biodegradable and non-biodegradable polymers, and more preferably, the biodegradable and non-biodegradable polymers may be selected from the group consisting of gelatin, polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polyurethane (PUR), polydimethylsiloxane (PDMS), silicone (SIL), polyethylene terephthalate (PETP), polytetrafluoroethylene (PTFE), and expanded polytetrafluoroethylene (ePTFE).

According to still another embodiment of the present invention, the functional material further may include at least one selected from the group consisting of a radiation marker, an anticancer agent, an antiinflammatory agent, and an antithrombotic agent.

Still more preferably, the radiation marker may be selected from the group consisting of gold (Au), platinum (Pt), silver (Ag), titanium (Ti), tantalum (Ta), niobium (Nb), molybdenum (Mo), rhodium (Rh), palladium (Pd), hafnium (Hf), tungsten (W), iridium (Ir), platinum-iridium (Pt—Ir), barium (Ba), barium sulfate ($BaSO_4$), cobalt (Co), and a mixture thereof. Also, the type of the radiation marker is various, such as a thin film, a rod, and a particle, and the size thereof may be freely used within a range which can be applied in a secure coating area proposed by the present invention.

Still more preferably, the anticancer agent is selected from the group consisting of cisplatin, carboplatin, oxaliplatin, procarbazine, mechlorethamine, cyclophosphamide, ifosfamide, melphalan, chlorambucil, bisulfan, nitrosourea, camptothecin, irinotecan, dactinomycin, carmustine, rapamycin, daunorubicin, doxorubicin, doxorubicin HCl, idarubicin HCl, bleomycin, plicomycin, mitomycin-C, etoposide, tamoxifen, paclitaxel, docetaxel, transplatinum, 5-fluorouracil, adriamycin, acvicin, aclarubicin, acodazole, ormaplatin, vincristin, vincristin sulfate, vinblastin, vinblastin sulfate, cytarabine, methotrexate, gemcitabine, gemcitabine HCl, capecitabine, and a mixture thereof.

Still more preferably, the antiinflammatory agent may be selected from the group consisting of aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenprofen, nambumetone (Relafen), acetaminophen (Tylenol), and a mixture thereof.

Still more preferably, the antithrombotic agent may be selected from the group consisting of aspirin, clopidogrel, indobufen, cilostazol, ticlopidine, beraprost, heparin, and a mixture thereof.

Advantageous Effects

Features and advantages of the present invention are summarized as follows:

(a) The present invention provides a stent having a cell area (secure coating area) coated with a functional coating material.

(b) According to the present invention, intensively considering a structure of a stent, an insertion tool, and a preparation process, for a functional coating implement technology applicable to an existing stent system other than the multi-layer coating method, an area in which a functional coating can be performed without increasing the deployment force required for the loading and withdrawal of the stent (secure coating area) were ensured through modeling.

(c) Conventionally, the stent is recognized as a single layer and the coating is conducted on the basis of the stent outer wall, whereas the stent of the present invention is coated targeting each cell area on the basis of a cell area defined as a secure coating area.

(d) According to the stent of the present invention, as a result of loading a radiation marker or a drug as a functional material in a secure coating area, the stent had no additional volume increase even when compressed and loaded in the delivery device, leading to a more excellent radiopaque effect without the interference of the loading and deployment of the stent, and it was confirmed through drug release profiles that a large amount of functional drugs can be securely loaded.

MODE FOR CARRYING OUT THE INVENTION

Hereinafter, a wire stent of the present invention will be described in detail with reference to the drawings, and examples presented below are only for illustrating the present invention more specifically, and thus, the scope of the present invention is not limited to the examples.

The present invention is directed to a stent having a cell area coated with a functional material.

Conventional coating techniques designed to allow a stent to ensure additional functionality are mainly directed to methods in which specific drugs or polymers are coated as a multi-layer on the stent while each coating layer performs a specific function or respective coating layers are allowed to well adhere and prevent the separation therebetween. However, the conventional techniques were designs in which the structure of a stent, an accompanying delivery device or catheter, and the preparation process were not sufficiently considered, and had a problem of being difficult to realize.

Therefore, the present inventors have studied a method for ensuring coating areas for loading drugs and other materials to expand the functions of a stent having a high possibility of realization as an actual product, intensively considering the structure of a stent, a delivery device, and the preparation process. As a result, as described later, the present inventors have ensured a coating area (secure coating area) for a functional material in a cell area of the stent through qualitative and quantitative modeling, and the present inventors have verified that, as a result of loading a radiation marker or a drug, as a functional material, in such a coating area, the stent had no additional volume increase even when compressed and loaded in the delivery device, leading to a more excellent radiopaque effect than existing ones, without the interference of the loading and deployment of the stent, and the present inventors have also verified through drug release profiles that a large amount of functional drugs can be securely loaded.

Hereinafter, qualitative and quantitative modeling procedures for ensuring a coating area (secure coating area) of a functional material in a cell area of a stent will be described in detail.

Qualitative Modeling

Figure 1:
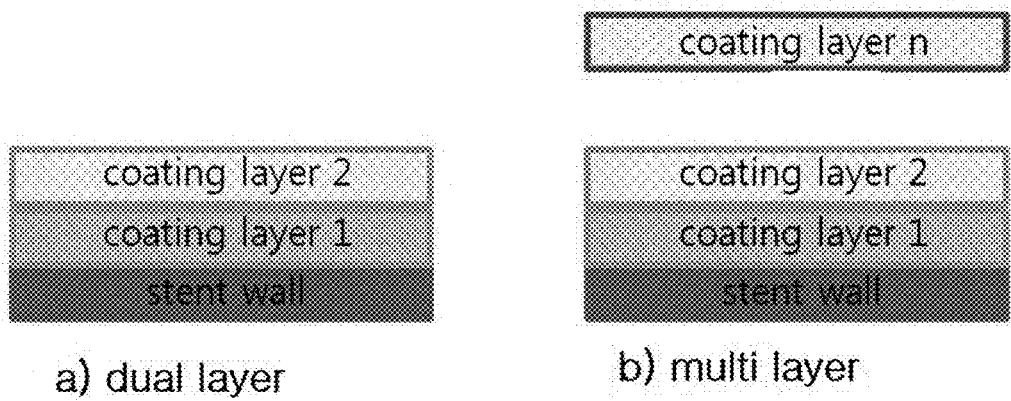
FIG. 1 shows structures of a dual-layer and a multi-layer formed by a conventional stent functional coating method.
Figure 2:
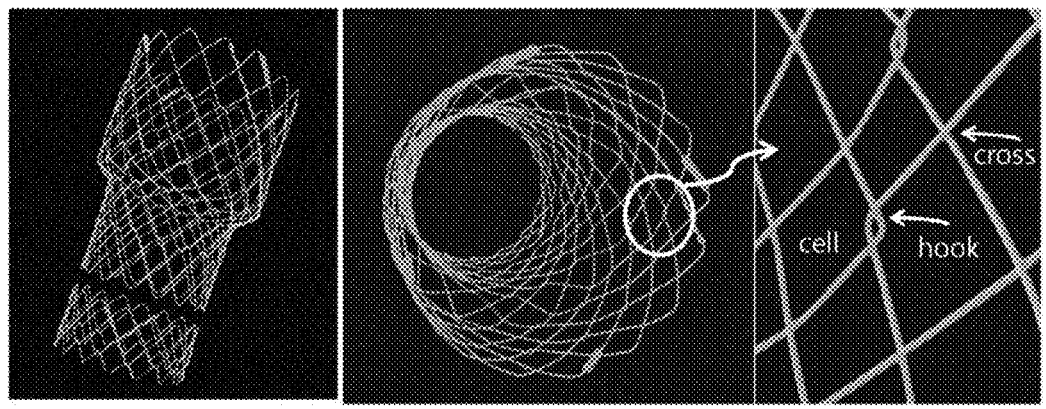
FIG. 2 shows a sectional structure of a stent with hooks and crosses formed by weaving a wire material.
Figure 3:
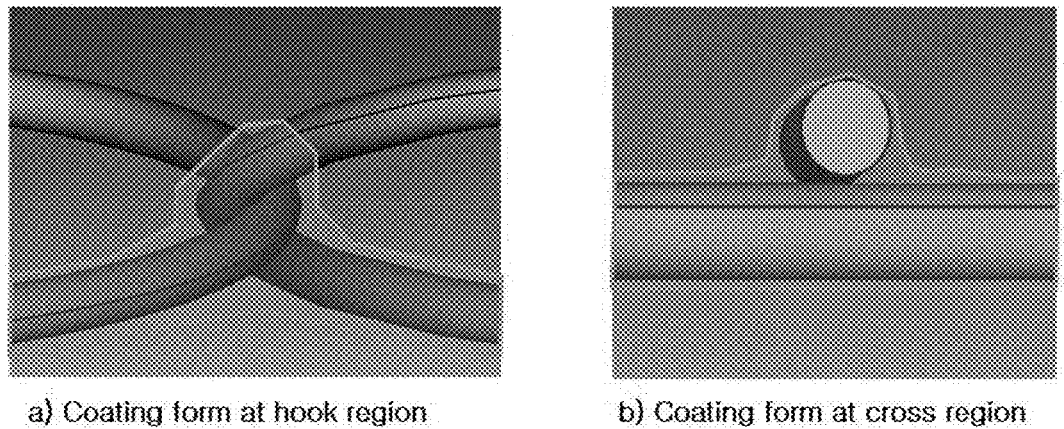
FIG. 3 shows coating forms formed at the outer periphery of a wire in a case of general external coating.
Figure 4:
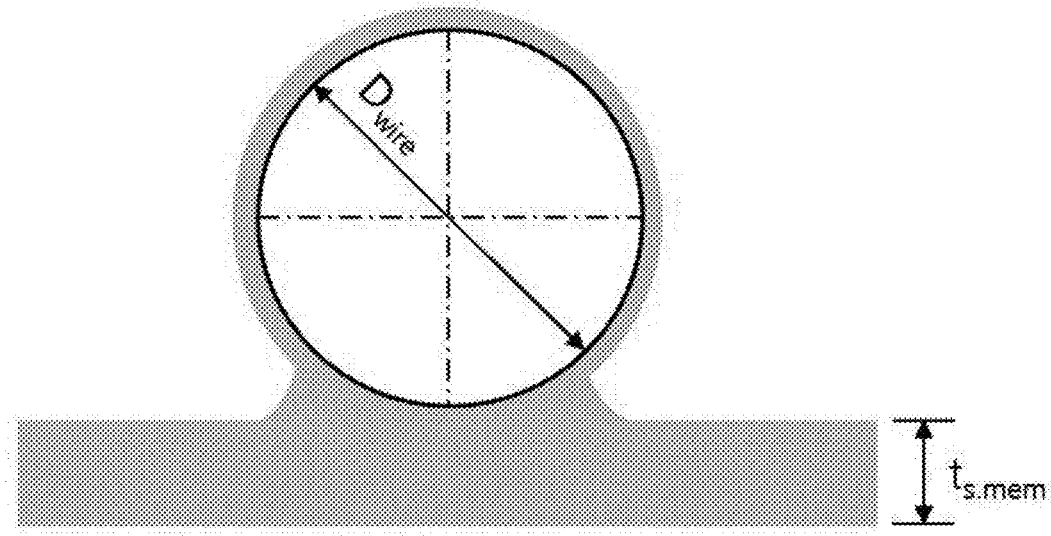
FIG. 4 shows a coating form of a section of one wire with respect to FIG. 3.
Figure 5:
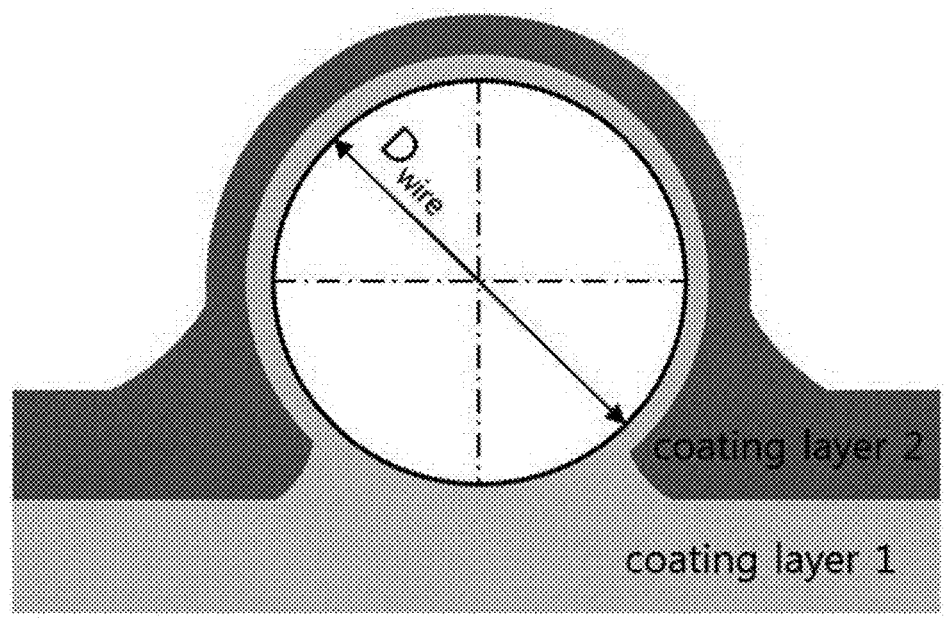
FIG. 5 shows a coating form of a dual-layer by conducting additional functional coating in the coating state shown in FIG. 4.
Figure 6:
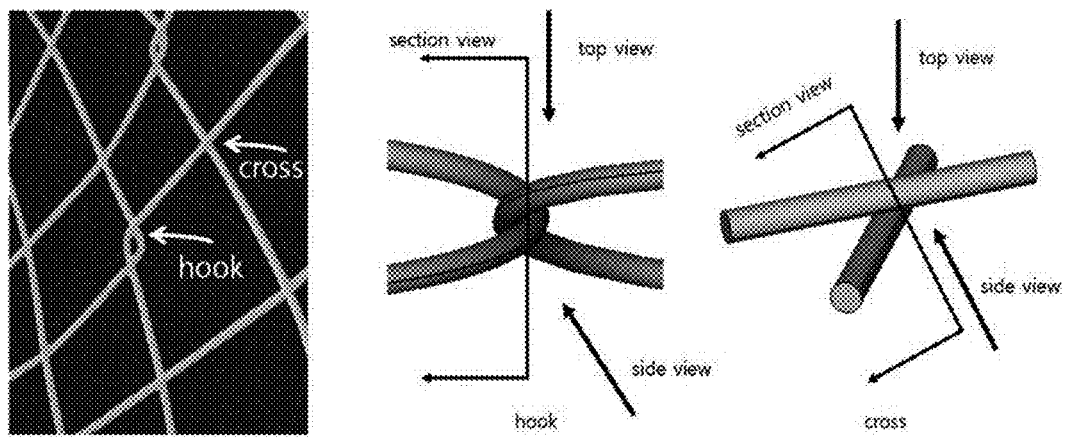
FIG. 6 shows schematic views of hook and cross models of a stent taken along three directions (top, side, section).
Figure 40:
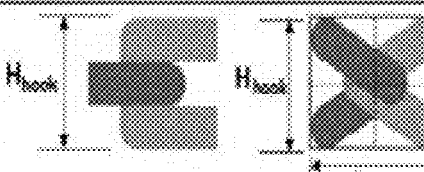
FIG. 40 shows hook and cross models of a stent.

Hook and cross models of a stent are depicted as follows according to the three directions of view (top, side, section) (FIG. 6 and FIG. 40).

A single stent formed by weaving a wire has many hooks and crosses, each of which acts as one connection point on a network, and therefore, each is defined as a node instead of the term "model".

A scale factor is a kind of marginal factor for avoiding the interference with neighboring hook and cross nodes in determining the physical height, width, and length of each node when a wire with a diameter of $\phi$ is used.

For example, the height, width, and length of a hook node are 0.3 mm, 0.33 mm, and 0.4 mm, respectively, for a wire with $\phi=0.1$ mm.

For hook and cross nodes, a cubic block is formed at each node based on the height, width, and length, reflecting the scale factor, to check the model interference with a neighboring node, and a portion without the model interference is defined as a "secure coating area".

Certainly, coating may be conducted allowing model interference in the actual preparation process, but for literally "secure" coating, the coating on the basis of the "secure coating area" is recommended more preferentially.

Specifically, the "interference area" may be classified into model interference and physical interference.

Figure 7:
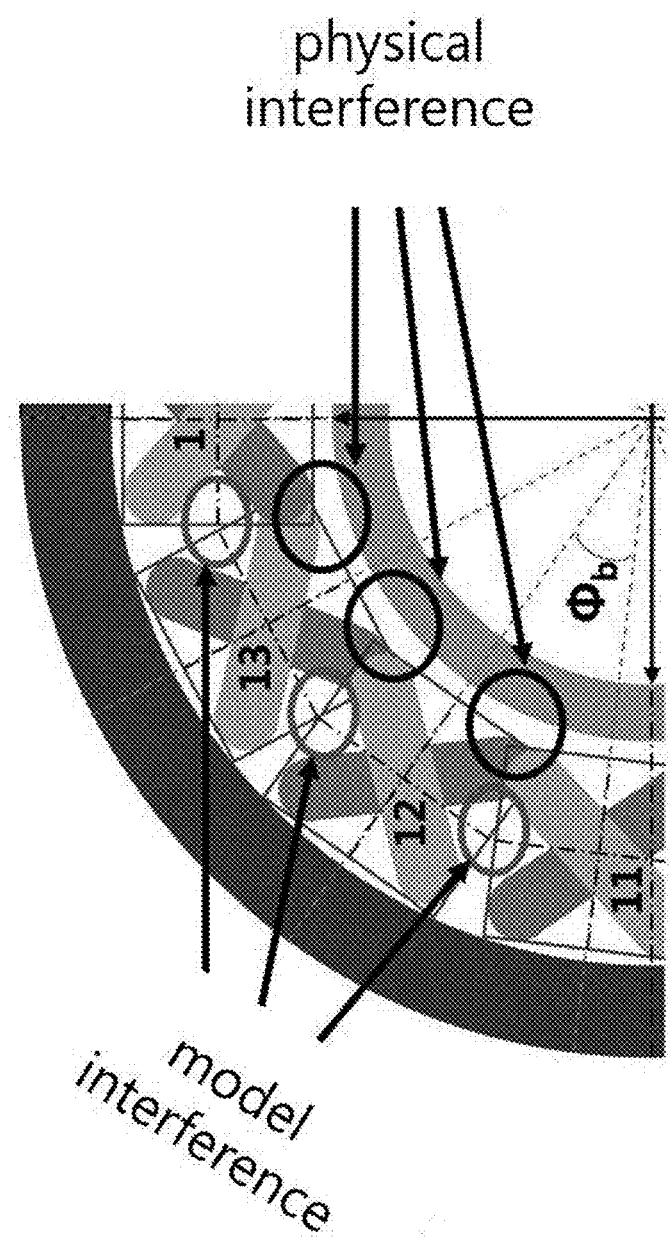
FIG. 7 shows interference areas at hook and cross nodes formed by a wire.

A model interference area means a kind of logical interference, occurring between cubic blocks when a cubic block considering a scale factor is applied to a node, and a physical interference area means an actual interference in which mutual physical contacts actually occur at the hook and cross nodes formed by an actual wire (FIG. 7).

Once a physical interference area occurs, a corresponding area is determined to be unsuitable as an additional functional coating area even when a secure coating area exists. Of course, in the actual preparation process, the coating may be compulsorily conducted while such a determination is ignored, but such coating is not recommended. However, if there is no physical interference area, a corresponding area can be coated even in the presence of a model interference area. Such a corresponding area may be called "coating allowed area" (FIG. 8).

Figure 8:
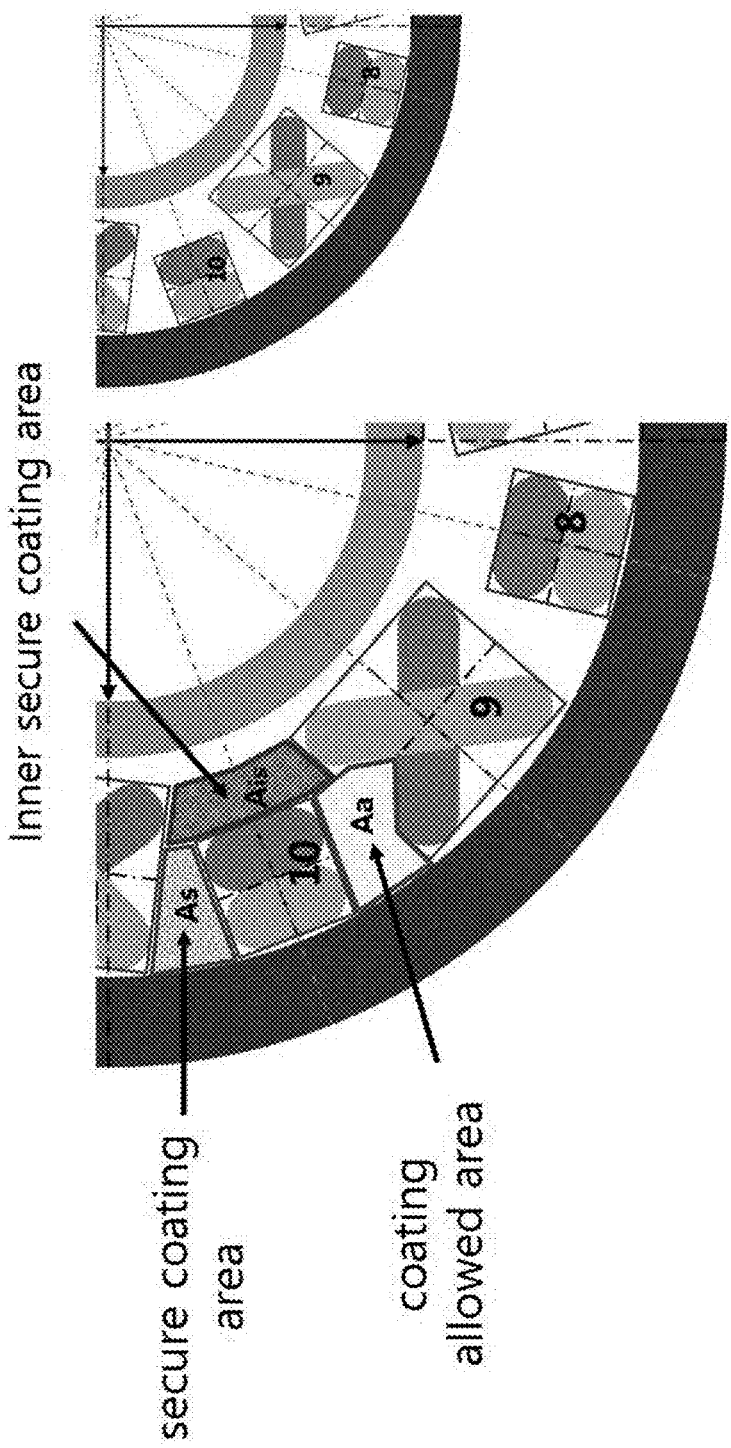
FIG. 8 shows a secure coating area and a coating allowed area.

When inner coating is conducted rather than stent outer wall coating, an "inner secure coating area" can also be ensured (FIG. 8).

Figure 9:
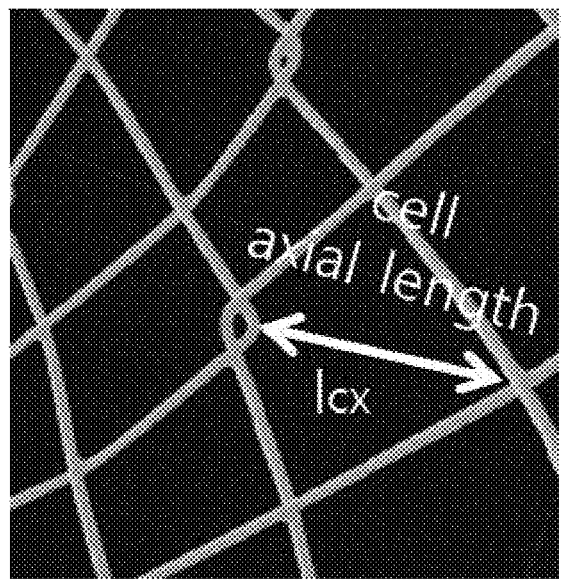
FIG. 9 shows the axial length of cell in a wire stent.

The coating volume entering the coating area is determined by approximately the coating area sectional area X the axial length of cell ($I_{cx}$), that is, $A \times I_{cx}$, according to the axial length of cell (FIG. 9).

As for the procedure in which node models (as shown in FIG. 40) are made and a stent is compressed and loaded (inserted) in a delivery device, when additional functional coating is conducted in a secure coating area, where there are no interference between mutual nodes and no interference with the inner wall of the delivery device, and then the stent is compressed and loaded in the delivery device, the stent can be securely loaded in the delivery device without an additional volume increase causing interferences, allow deployment, and ensure desired additional functionality.

Especially when the stent is compressed and loaded in a delivery device during the preparation process, the stent is pushed in or pulled out, and in such a procedure, the stent coating is highly likely to be damaged, such as separation, cracking, and breakage, but the coating in the secure coating area can avoid physical damages.

An example of ensuring a secure coating area or a coating allowed area using the node model is as follows.

Assuming that a stent with a wire diameter of 0.12 mm, six hooks, and seven crosses, which are crossed at a constant angle with each other, is loaded in a delivery device with an outer diameter of 7.2 fr (2.38 mm), a method for ensuring a secure coating area will be described. It is assumed that the thickness of the delivery device is 0.17 mm, and the outer diameter of the tube located inside the delivery device is 1.22 mm.

Figure 10:
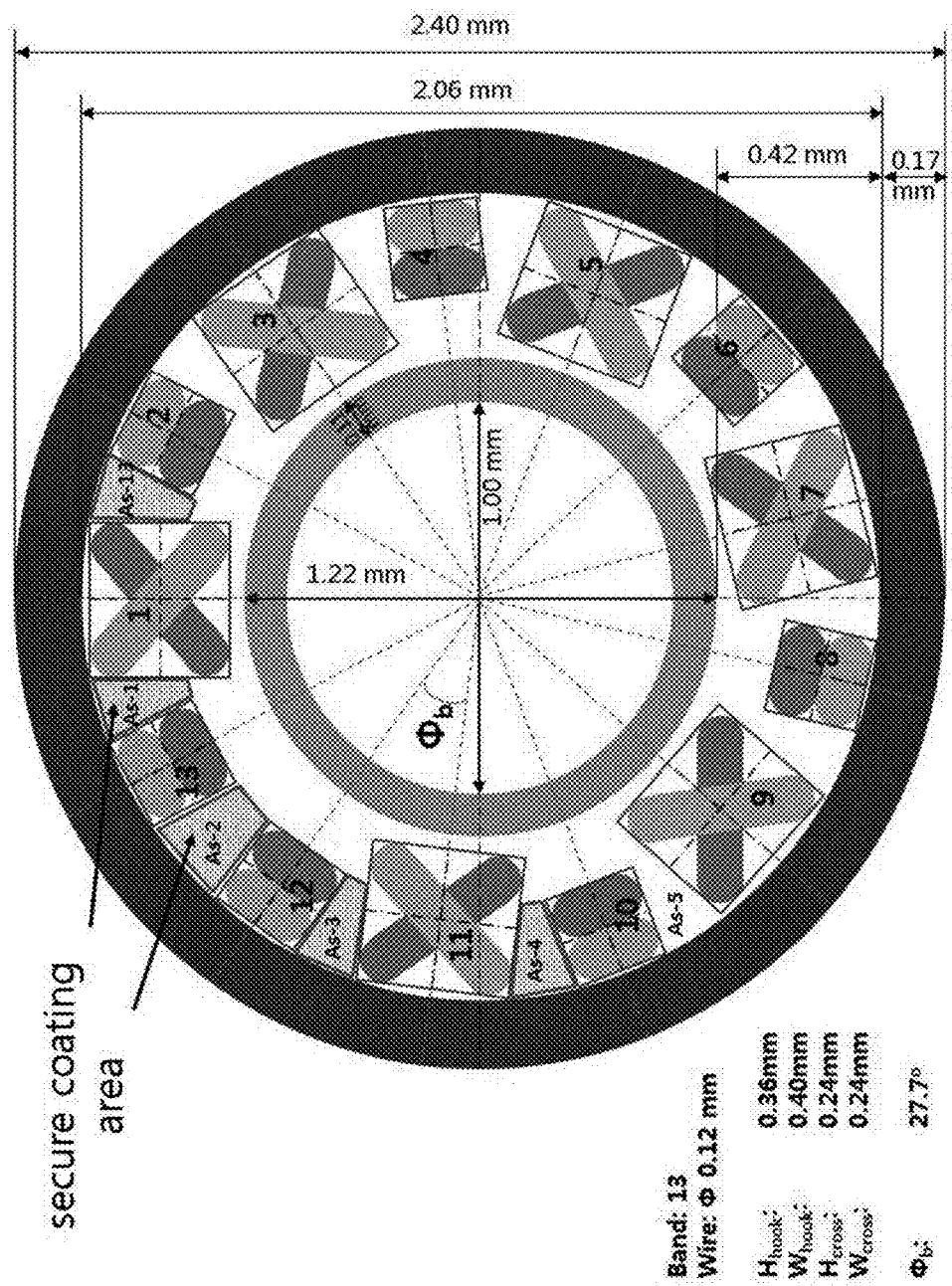
FIG. 10 shows a schematic view of a state in which a stent is loaded in a delivery device while hook and cross nodes of the wire stent are compressed.

FIG. 10 is a schematic diagram of a situation in which hook and cross nodes are compressed and loaded inside the delivery device, and 13 secure coating areas with a size of about 70 μm in width and 240 μm in length can be confirmed to be ensured.

Figure 11:
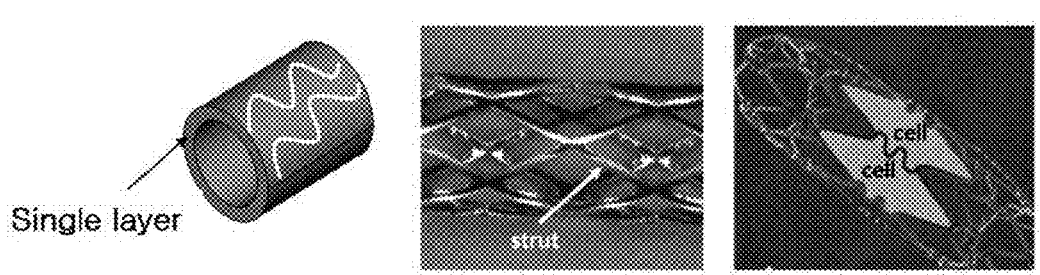
FIG. 11 shows a stent tube formed by struts and cells while the tube has a thickness of a single layer.
Figure 12:
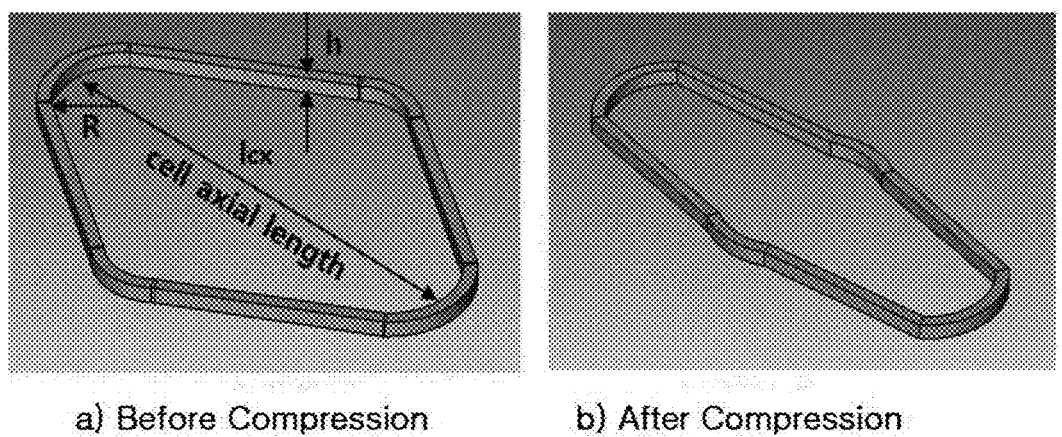
FIG. 12 shows a secure coating area in a tube stent.

The concept of a secure coating area can be equally applied to a stent formed by weaving a wire material as well as a tube stent prepared by a laser cutting process. The tube stent has struts and cells while having a thickness of a single layer (FIG. 11). The strut vertex has a specific radius of cell axial end R, which is applied at the time of design, and even when the stent is compressed in a balloon catheter or the like, the stent has at least R, the cell axial length ($I_{cx}$), and height (h) corresponding to the thickness, thereby ensuring a secure coating area with approximately $2R \times (I_{cx}-2R) \times h$ can be ensured (FIG. 12).

Quantitative Modeling

There are some differences in the approach to quantitative equation modeling of the secure coating area between a wire woven stent and a tube stent. The biggest one is a difference in the degree of freedom of movement at each node.

In the case of the wire woven stent having a hook and a cross as a basic node, the left and right, up and down, and rotation movements of the node are freer than those of the node of the tube stent, and thus, although limited, a secure coating area is variably changeable.

For example, a secure coating area and an inner secure coating area are outer and inner areas, respectively, but both are not fixed areas but movable areas to be movable to the inner secure coating area, and thus, any one area can be maximized and utilized according to the purpose of functional coating.

Figure 13:
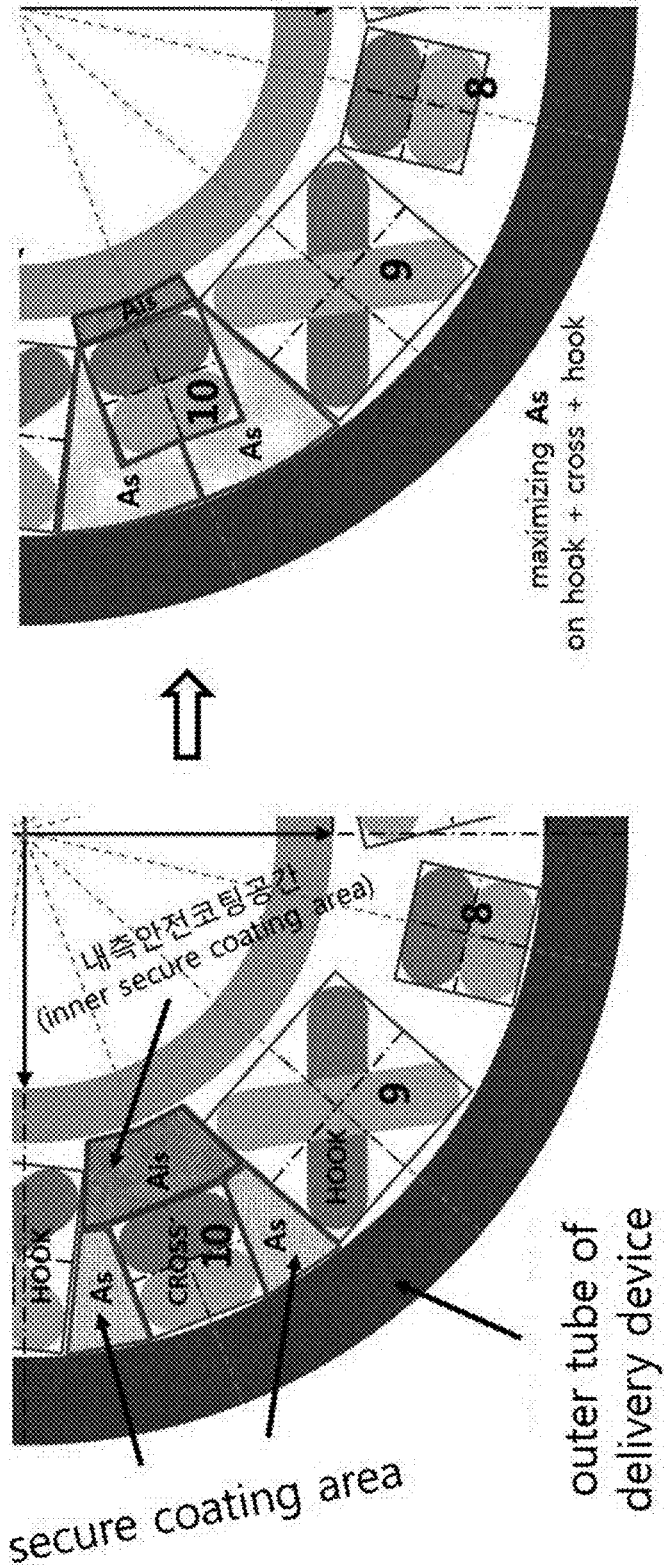
FIG. 13 shows a secure coating area and an inner secure coating area in a wire stent formed in the order of hook+cross+hook.
Figure 14:
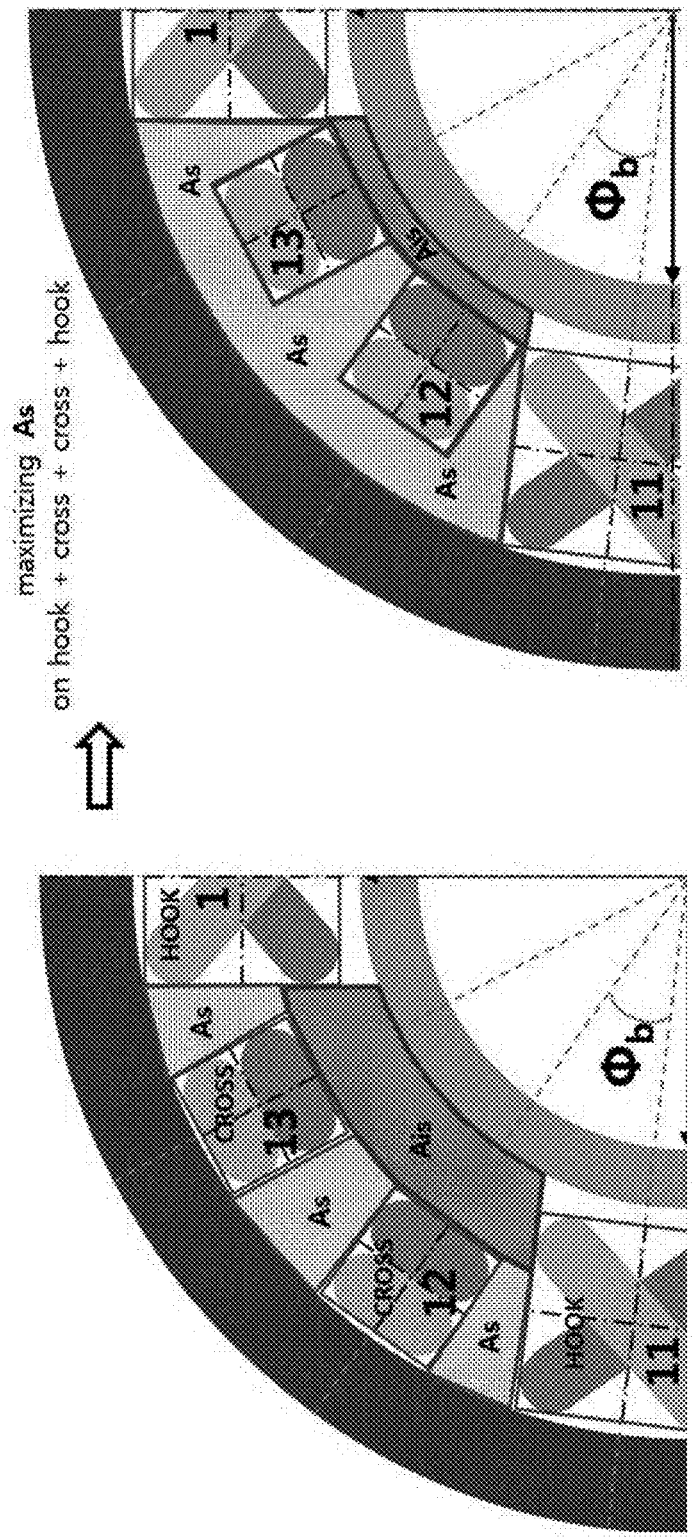
FIG. 14 shows a secure coating area and an inner secure coating area in a wire stent formed in the order of hook+cross+hook.

FIG. 13 shows a secure coating area and an inner secure area when the stent has hook+cross+hook in that order, and FIG. 14 shows a secure coating area and an inner secure area when the stent has hook+cross+cross+hook in that order.

Therefore, the quantitative modeling of the secure coating area of the wire woven stent having hooks and crosses will be modeled assuming that, for convenience, the secure coating area is maximized, in the absence of physical and model interference.

The basic parameters associated with the secure coating area of the wire woven stent are: wire diameter ($D_w$), number of hooks per section ($N_h$), number of crosses per section ($N_c$), axial length of cell ($I_{cx}$), inside diameter of delivery device ($D_i$), and shortening ratio ($r_{short}$).

Figure 15:
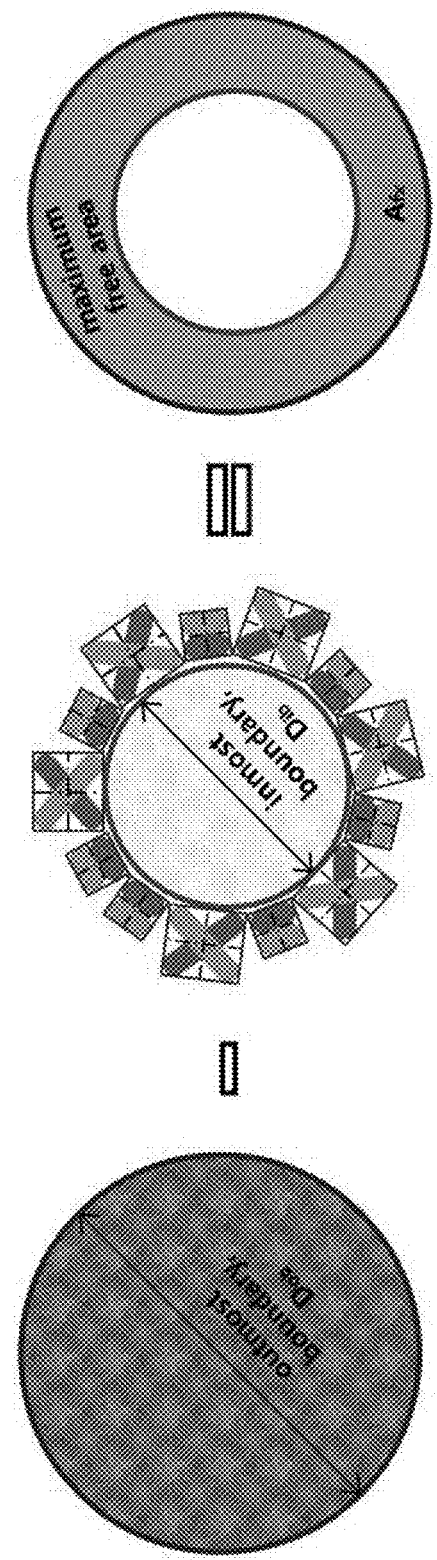
FIG. 15 shows a maximum free area ($A_{fx}$) according to the boundary condition.

As can be seen from FIGS. 13 and 14, the sectional shape of the secure coating area is slightly different according to the arrangement structure of the hooks and the crosses, and thus, instead of calculating an individual secure coating area at each node, the boundary condition satisfying the conditions without physical and model interference is set, and then the boundary inner area is called the maximum free area ($A_{fx}$, FIG. 15), and when the hook and cross node area ($A_{nd}$) existing in the maximum free area is excluded, the remaining area is the maximum secure coating area ($A_{sx}$).

Figure 16:
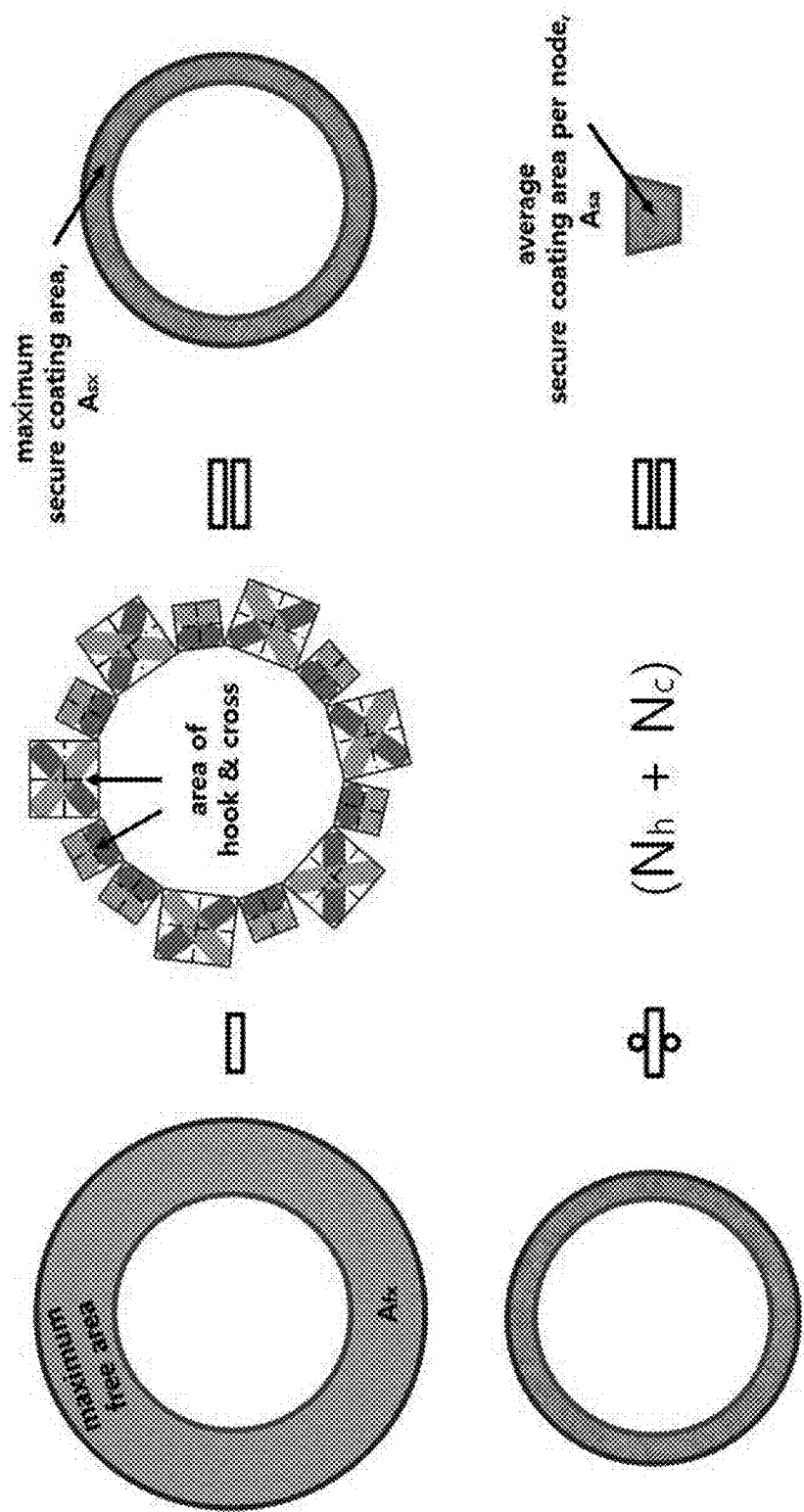
FIG. 16 shows a maximum secure coating area ($A_{sx}$) according to the boundary condition.

The average secure coating area per node can be obtained by dividing the maximum secure coating area ($A_{sx}$) by the total number of nodes per section ($N_t$, $N_t=N_h$, $N_c$), that is, $A_{sa}=A_{sx}/N_t$ (FIG. 16).

Figure 17:
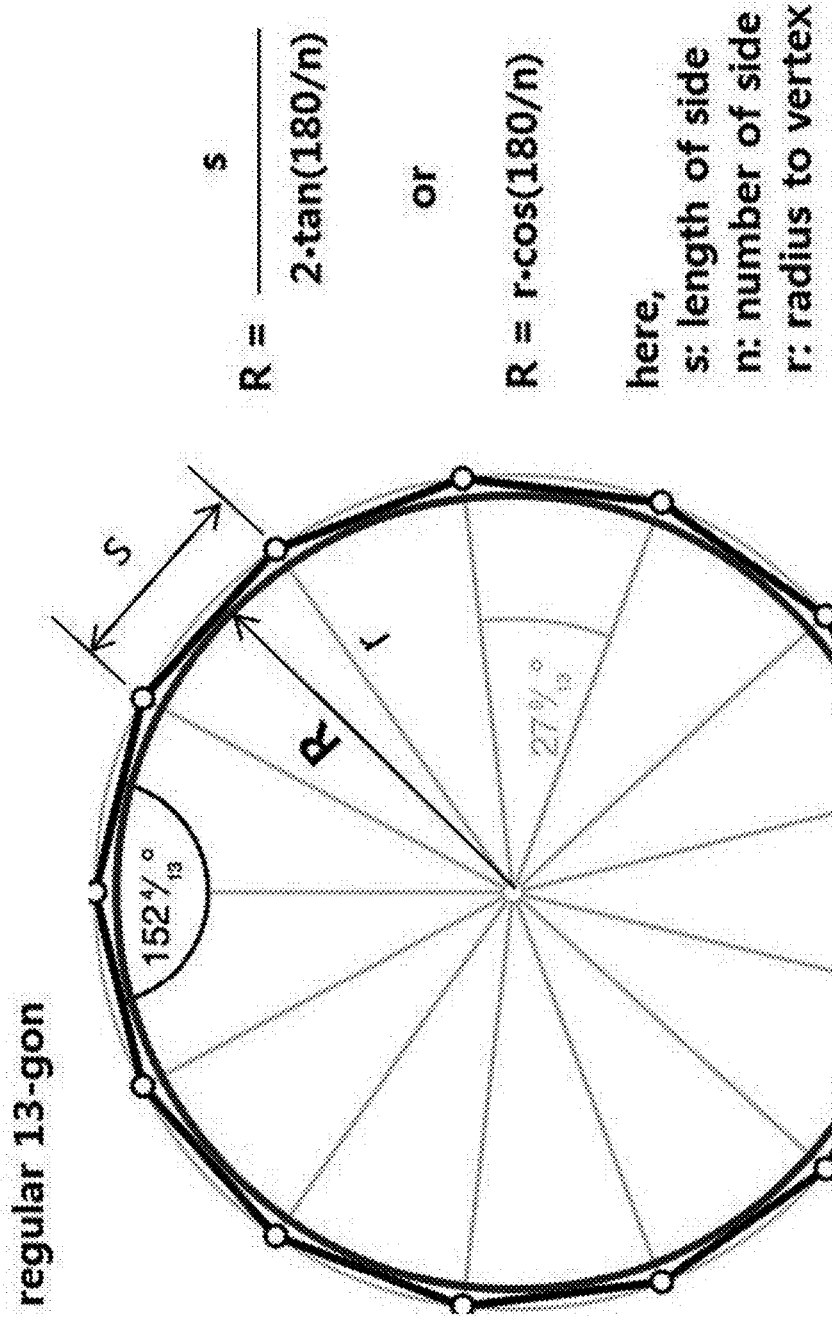
FIG. 17 shows the inradius of a regular polygon when the bottom side of hooks is equal to that of crosses.
Figure 18:
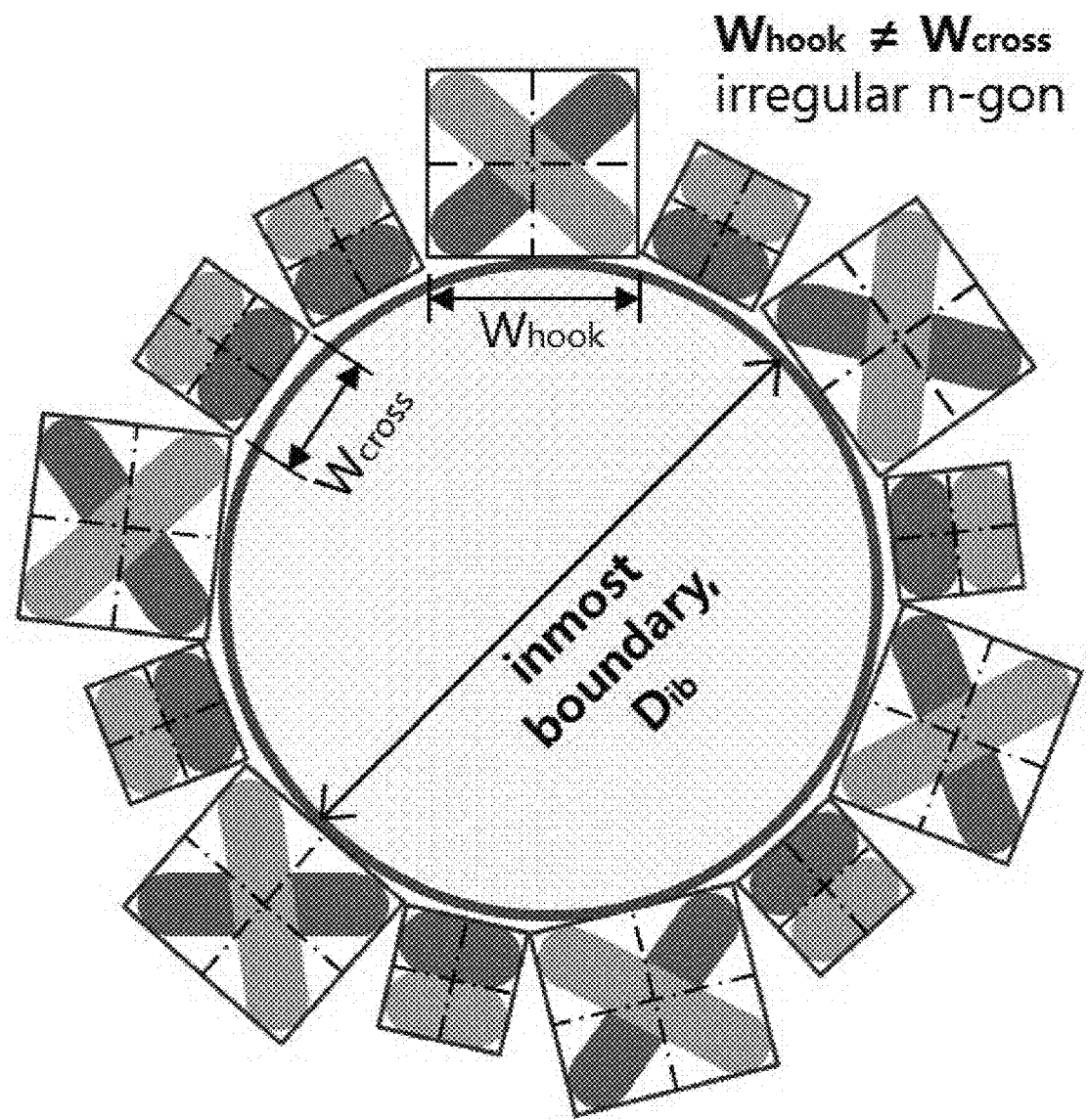
FIG. 18 shows an irregular polygon when the bottom side of hooks is not equal to that of crosses.

The boundary condition can be obtained as follows:

First, the inmost boundary ($D_{ib}$) is, theoretically, the same as the circumference of the incircle of a polygon formed when the hook and cross nodes existing on the section of the wire woven stent are maximally compressed in a radial direction without physical and model interference. In a regular polygon in which the bottom sides of the hook and the cross are equal to each other, the radius of the incircle can be easily obtained (FIG. 17), but the present model in which the bottom sides of the hook and the cross are not equal to each other is an irregular polygon (FIG. 18), and thus, the radius of the incircle is difficult to mathematically express.

However, the bottom sides of the polygon used in the present model have two types, that is, only a hook and a cross, and thus, the present polygon is not a very irregular polygon but an irregular polygon that forms two kinds of regular polygons.

Figure 19:
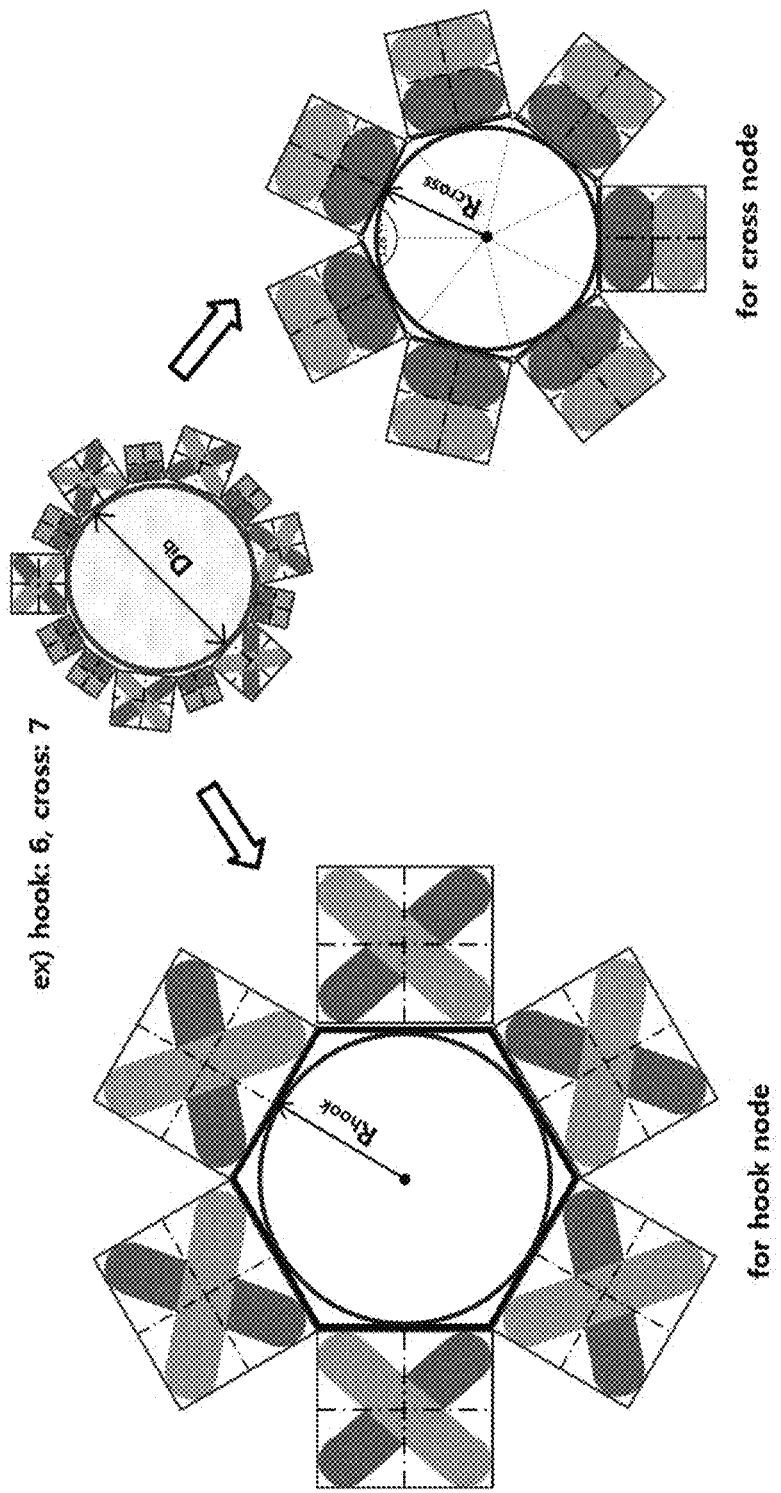
FIG. 19 shows a model of the present invention of an irregular polygon forming two types of regular polygons according to the hook and cross.

Therefore, the centers of the circles inscribed in the respective regular polygons are the same. That is, the respective polygons have the same incircle center (FIG. 19), and the compression in the radial direction is conducted toward the same incircle center.

When the concept of an average nominal width ($W_{avg}$) is applied to the bottom side (nominal width) of hook ($W_{hook}$) and the bottom side of cross ($W_{cross}$) considering the above characteristics, a nominal regular polygon can be obtained, and thus the radius of the incircle can be easily obtained.

The average nominal width ($W_{avg}$) is the value obtained by dividing the sum total of nominal width of hook and cross nodes ($W_{total}$) applied to the section of the wire woven stent by the total number of hook and cross nodes ($N_t$). That is, $$W_{avg} = \frac{W_{total}}{N_t} = \frac{(W_{hook} \times H_h + W_{cross} \times N_c)}{(N_h + N_c)}.$$

Figure 20:
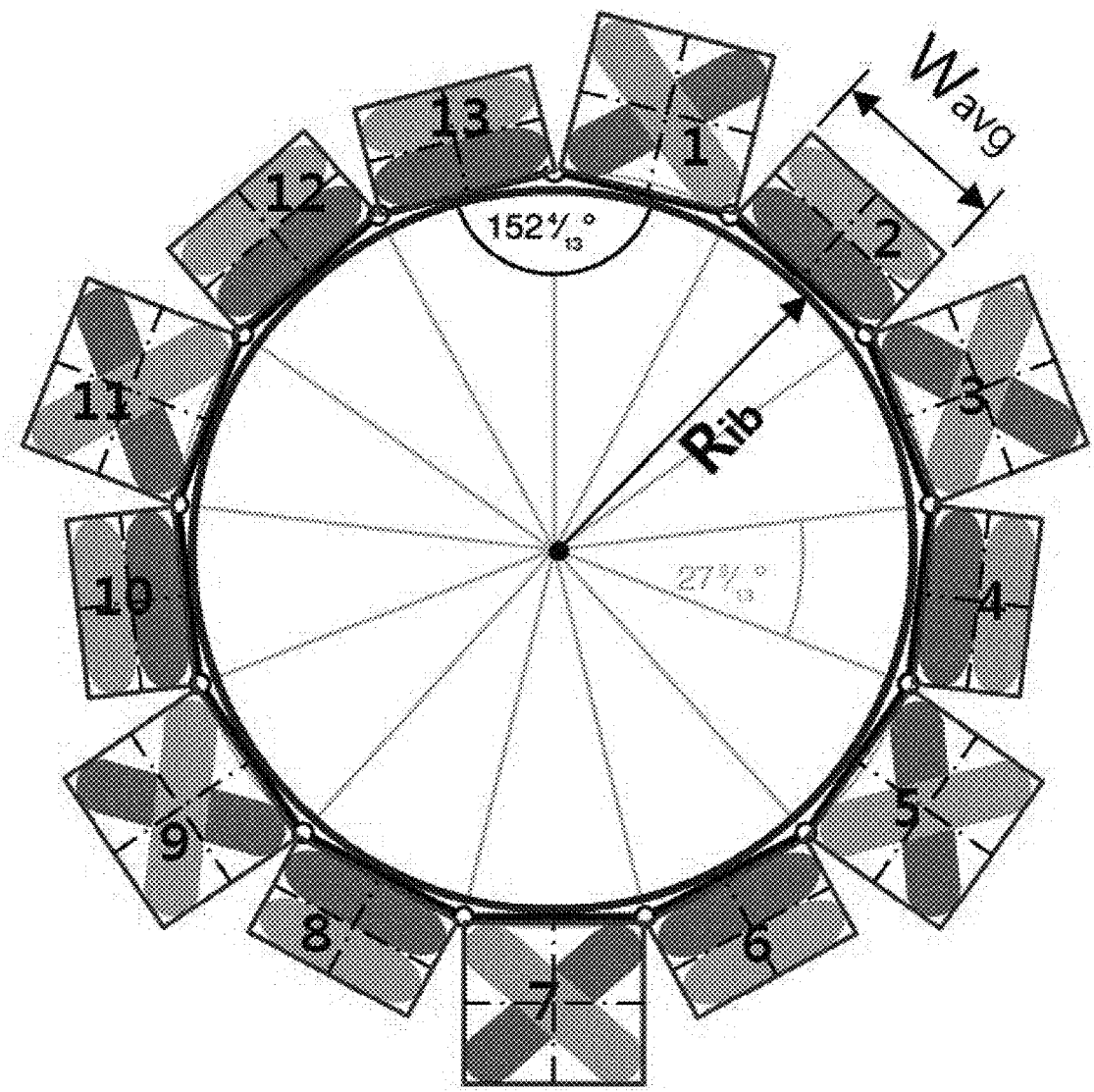
FIG. 20 shows a nominal regular polygon obtained by applying the concept of an average nominal width ($W_{avg}$) to the bottom side (nominal width) of hook ($W_{hook}$) and the bottom side of cross ($W_{cross}$).

When the average nominal width ($W_{avg}$) is applied to an example (hook: 6, cross: 7), an incircle can be exactly configured as shown in FIG. 20, and here, the radius of the incircle ($R_{ib}$) configuring the inmost boundary ($D_{ib}$) is as follows:

$$R_{ib} = \frac{W_{avg}}{2 \cdot \tan(180/N_t)},$$

here, $N_t=(N_h+N_c)$.

Here, the length of the circumference, $S_{ib}$, configured by the radius of the incircle, $R_{ib}$, should be smaller than or equal to the sum total of nominal width of nodes, $W_{total}$.

That is, $S_{ib}=R_{ib} \leq W_{total}$

The above equation can be derived from $\pi/(N_t \tan(180/N_t)) \leq 1$, and is always established at $Nt \geq 3$, the minimum polygon condition.

The following is a method for determining the outmost boundary ($D_{ob}$).

Figure 21:
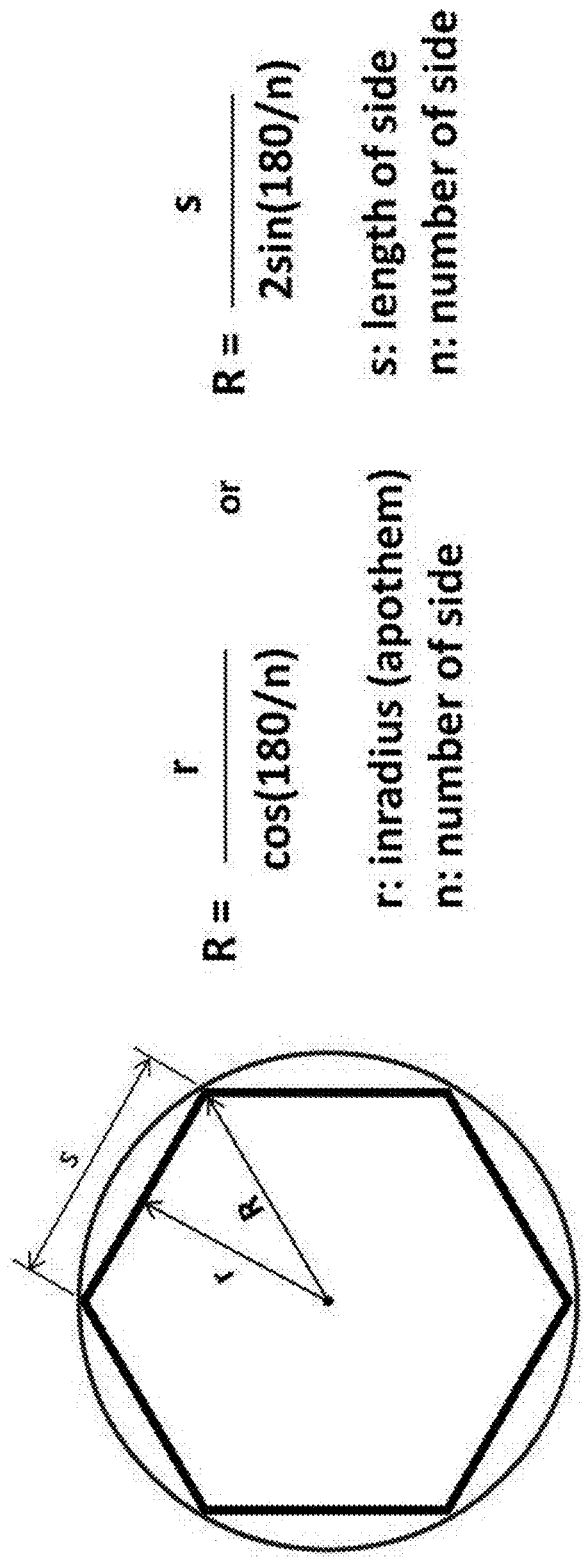
FIG. 21 shows the outmost boundary ($D_{ob}$) determined by obtaining the circumcircle in similar manner to the innermost boundary ($D_{ib}$) in a regular polygon.

The outermost ($D_{ob}$) can be used to obtain the circumcircle in a similar manner to the inmost boundary ($D_{ib}$) (FIG. 21), but the outermost boundary does not form a regular polygon like when the inmost boundary is determined, and thus, the formatted analytical equation of the outermost boundary is difficult to express.

Figure 22:
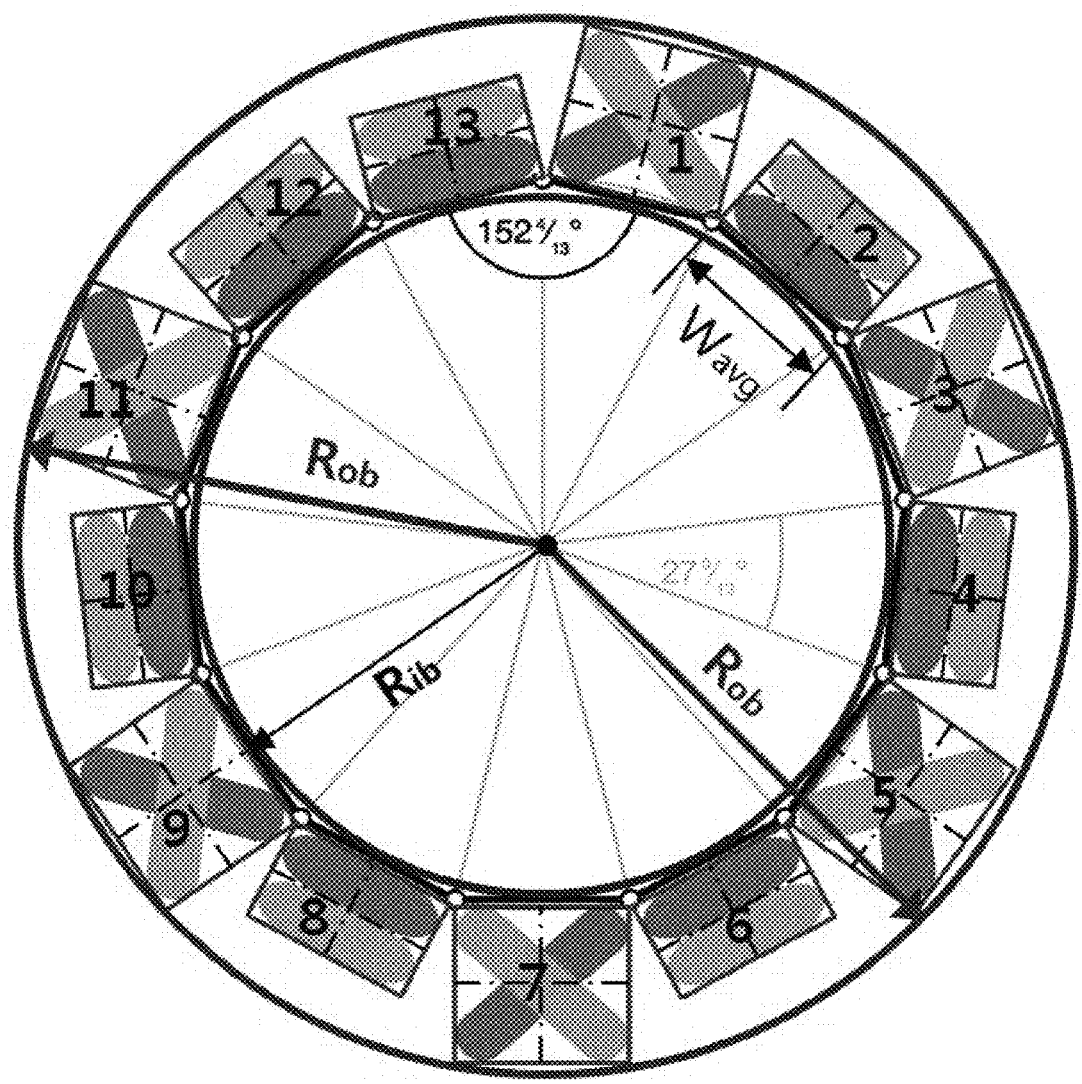
FIG. 22 shows the outmost boundary ($D_{ob}$) determined at only hook nodes with a large nominal height.

However, the outermost boundary ($D_{ob}$) needs to be determined at only the hook node having a large nominal height. Under the application of the average nominal width ($W_{avg}$), the distances ($R_{ob}$) from the center of the incircle (that is, the incenter) to respective vertexes of the hook nodes are equal, and thus, there exists a circumcircle that passes through the respective vertexes, and here, the center of the circumcircle (that is, the circumcenter) is the same as the incenter (FIG. 22).

Figure 23:
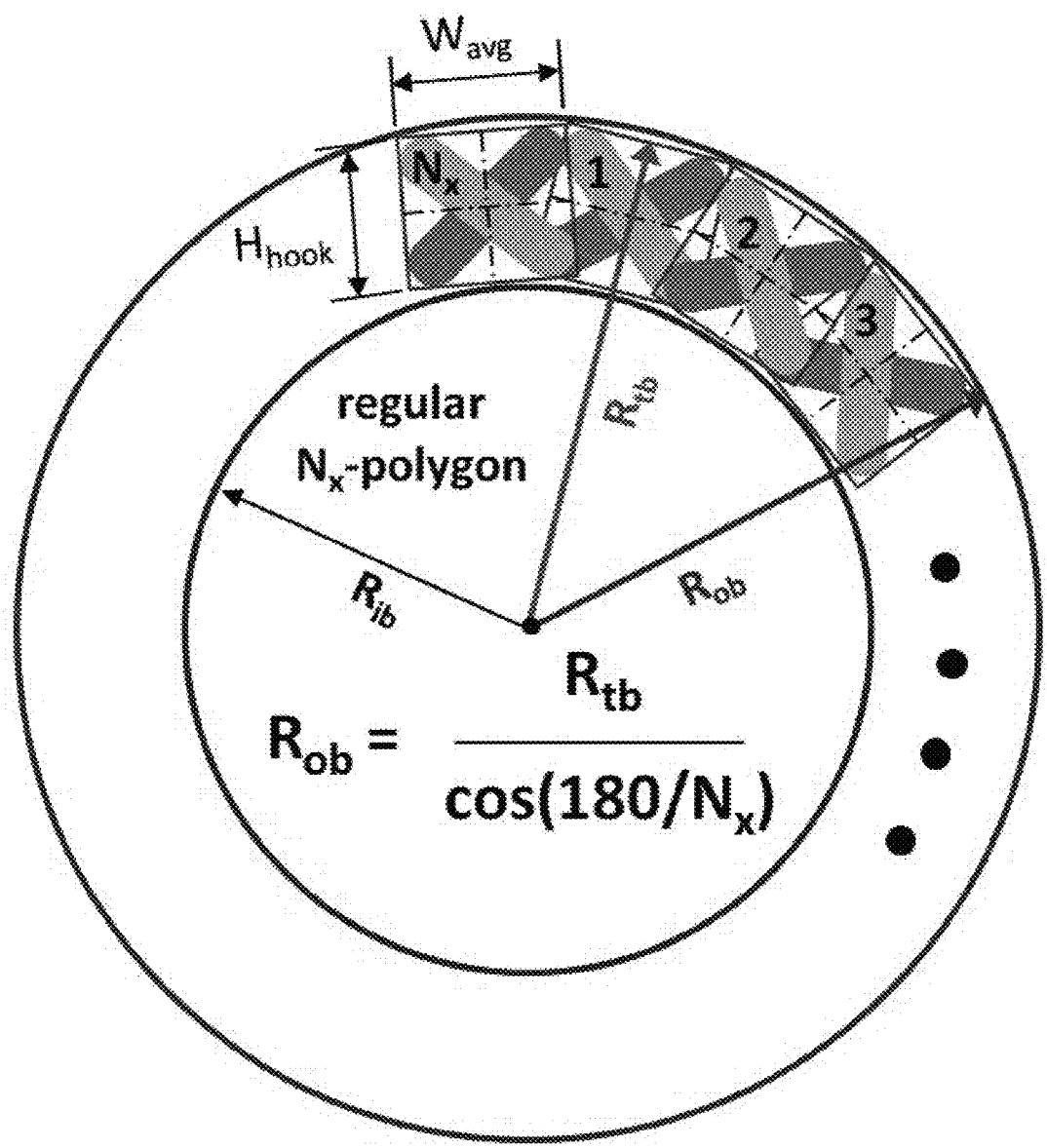
FIG. 23 shows the radius of outmost ($R_{ob}$) obtained through the number of sides formed by hook nodes with a length of $W_{avg}$ tangential on the circumcircle and the inradius of outmost boundary ($R_{tb}$).

Therefore, the radius $R_{ob}$ of the circumcircle for a regular $N_x$-polygon can be easily obtained if only the number of sides formed by hook nodes with a length of $W_{avg}$ tangential on the circumcircle ($N_x$) and the inradius of outmost boundary or the side-center distance ($R_{tb}$) are given (FIG. 23).

Figure 24:
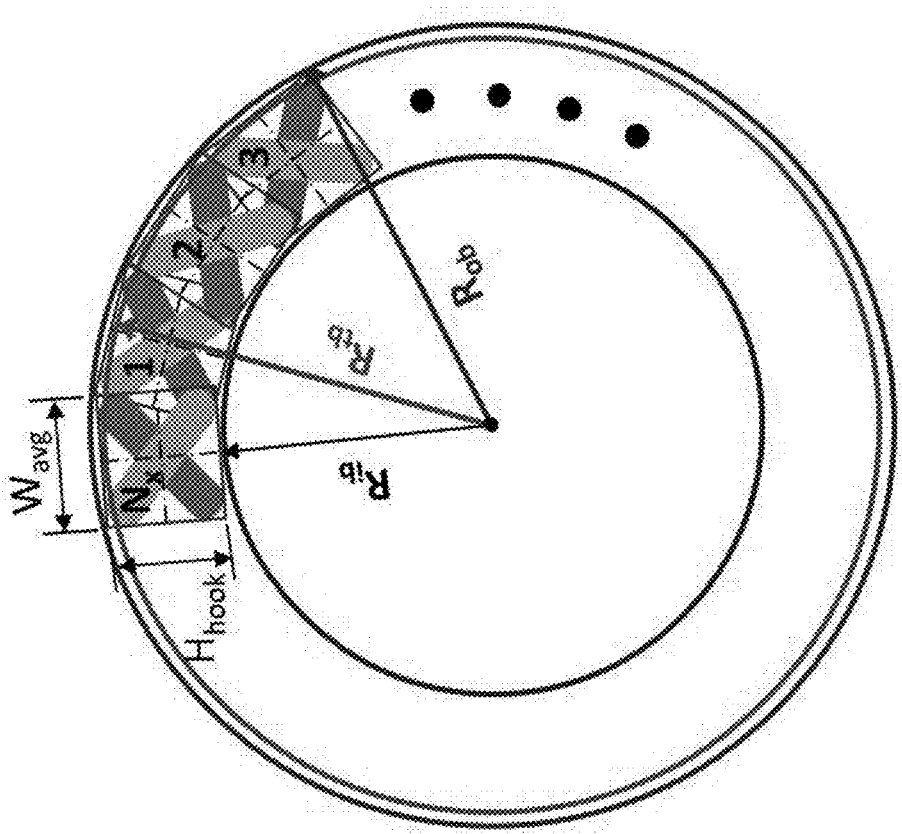
FIG. 24 shows the number of sides tangential on hook nodes, obtained from the inradius ($R_{tb}$) according to the presence of the incircle.

Specifically, together with FIG. 23, the incircle as well as the circumcircle exists for the hook nodes (FIG. 24), the number of sides tangential on the hook nodes, $N_x$, can be obtained from the radius of the incircle (inradius, $R_{tb}$) as follows:

$$R_{tb} = \frac{W_{avg}}{2 \cdot \tan(180/N_x)}$$

$$N_x = \left\| \frac{180}{\tan^{-1}(W_{avg}/(2R_{tb}))} \right\|,$$

here, $R_{tb}=R_{ib}+H_{hook}$.

Since $N_x$ is an integer, the round to the nearest integer number can be chosen.

The radius of the circumcircle, $R_{ob}$, configuring the outmost boundary ($D_{ob}$) can be obtained from the $N_x$ and $R_{tb}$ values obtained above. However, $R_{ib}<R_{tb}<R_{ob}$ condition needs to be satisfied $$R_{ob} = \frac{R_{tb}}{\cos(180/N_x)}$$

Here, the following conditions are satisfied for the circumcircle ($R_{ob}$) and the incircle ($R_{tb}$) tangential on the hook nodes:

a) The length of the circumference, $S_{ob}$, configured by the radius of the circumcircle, $R_{ob}$, should be greater than or equal to the sum total of nominal width of hook nodes, $W_{avg} \times N_x$. That is, $S_{ob}=2\pi R_{ob} \geq W_{avg} \times N_x$ b) The length of the circumference, $S_{tb}$, configured by the radius of the incircle, $R_{tb}$, should be smaller than or equal to the sum total of nominal width of hook nodes, $W_{avg} \times N_x$. That is, $S_{tb}=2\pi R_{tb} \leq W_{avg} \times N_x$ Nx should satisfy the following conditional expression from these two conditions.

$$\left\| \frac{2\pi R_{tb}}{W_{avg}} \right\| \leq N_x \leq \left\| \frac{2\pi R_{ob}}{W_{avg}} \right\| \quad (R_{tb} = R_{ib} + H_{hook})$$

When $(R_{ob}-R_{tb}) \ll H_{hook}$, the following condition is established, and thus, the value can be obtained from only $N_x=\|2\pi R_{tb}/W_{avg}\|$.

$$\frac{180}{\tan^{-1}(W_{avg}/(2R_{tb}))} \approx \frac{2\pi R_{tb}}{W_{avg}}$$

The area occupied by hook and cross nodes ($A_{nd}$, node area) can be simply obtained as follows:

$$A_{nd} = (W_{hook} \times H_{hook} \times N_h) + (W_{cross} \times H_{cross} \times N_c)$$

Therefore, the maximum secure coating area ($A_{sx}$) is as follows:

$$A_{sx} = \pi(R^2_{ob} - R^2_{ib}) - A_{nd}$$

The average secure coating area per node ($A_{sa}$) is defined as follows:

$$A_{sa} = A_{sx}/N_t, (N_t = N_h + N_c)$$

If the inner diameter of the delivery device ($D_i$) in which the stent is loaded is greater than the outmost boundary ($D_{ob}$), then $R_{ob} = R_i = D_i/2$, and thus, the average secure coating area per node ($A_{sa}$) can be further increased.

The average secure coating area per node ($A_{sa}$) is an area for a section of a stent having hook and a cross nodes (that is, a section area), and thus, in order to obtain the average secure coating volume per node ($V_{sa}$) coated in a cell area, the deformation of the plane area of cell due to the compression of the stent and the loading of the stent in the delivery device should be considered.

The plane shape of cell in the wire woven stent may be a diamond shape, a pentagonal shape, a hexagonal shape, or the like, but is generally a rhomboid shape, which is favorable in view of a compression rate.

Figure 25:
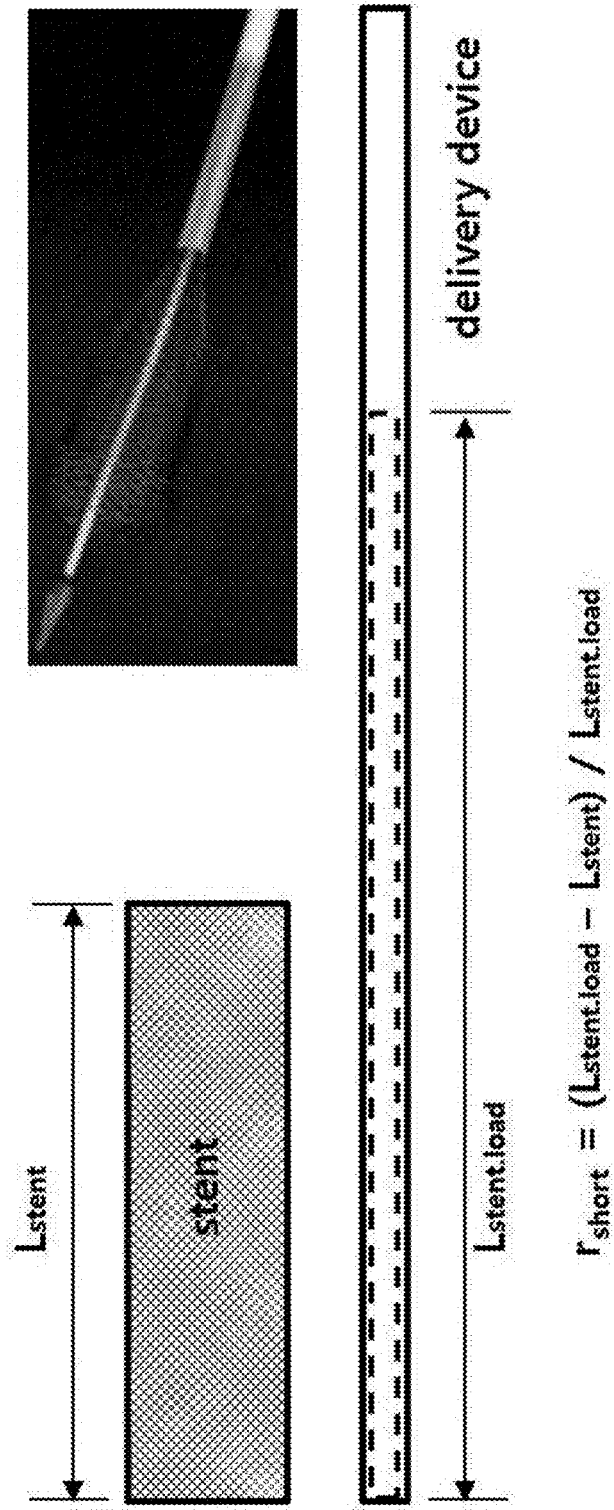
FIG. 25 shows the shortening rate or shortening ratio considering when a wire stent is loaded in a delivery device.

When a wire woven stent with a large diameter is loaded in a delivery device with a small diameter (<⅕), the length of the stent becomes longer than the original length thereof. This phenomenon is called shortening rather than extending. Regarding the origin of the term, from the viewpoint of a user, that is, a doctor, the stent, which is loaded long in the delivery device, normally returns to its original length when withdrawn, but from the viewpoint of a viewer, the viewer gets a feeling of shortening, and thus, the term shortening is used, and the shortening rate or shortening ratio is used as one of the performance evaluation factors of a stent (FIG. 25).

The shortening ratio ($r_{short}$) has a value in the range of approximately 0.2-0.6 according to the shape of the cell applied to the stent, the positions and arrangement structures of hooks and crosses, and the inner diameter of the delivery device.

Figure 26:
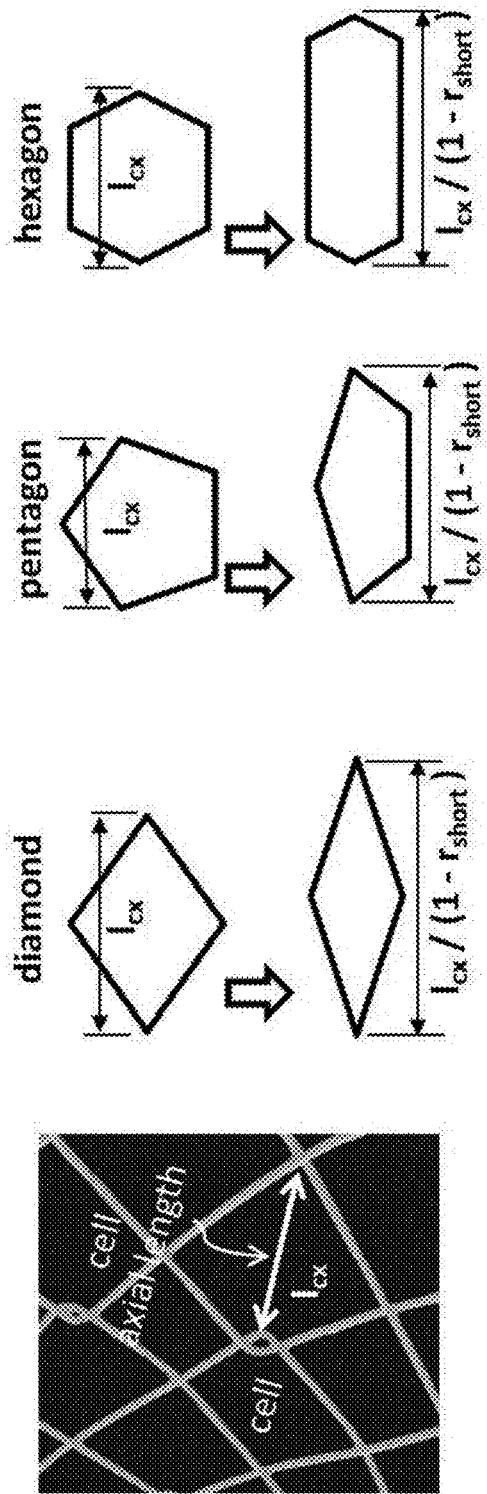
FIG. 26 shows quantified modifications of a plane area of cell according to the loading in a delivery device regardless of the shape of cell.

Therefore, the deformation of the plane area of cell according to the loading in the delivery device can be quantified as follows using the axial length of cell ($I_{cx}$) and the shortening ratio ($r_{short}$) irrespective of the shape of the cell (FIG. 26).

$$r_{short} = (I_{cx.load} - I_{cx})/I_{cx.load}$$

$$I_{cx.load} = I_{cx}/(1 - r_{short})$$

Figure 27:
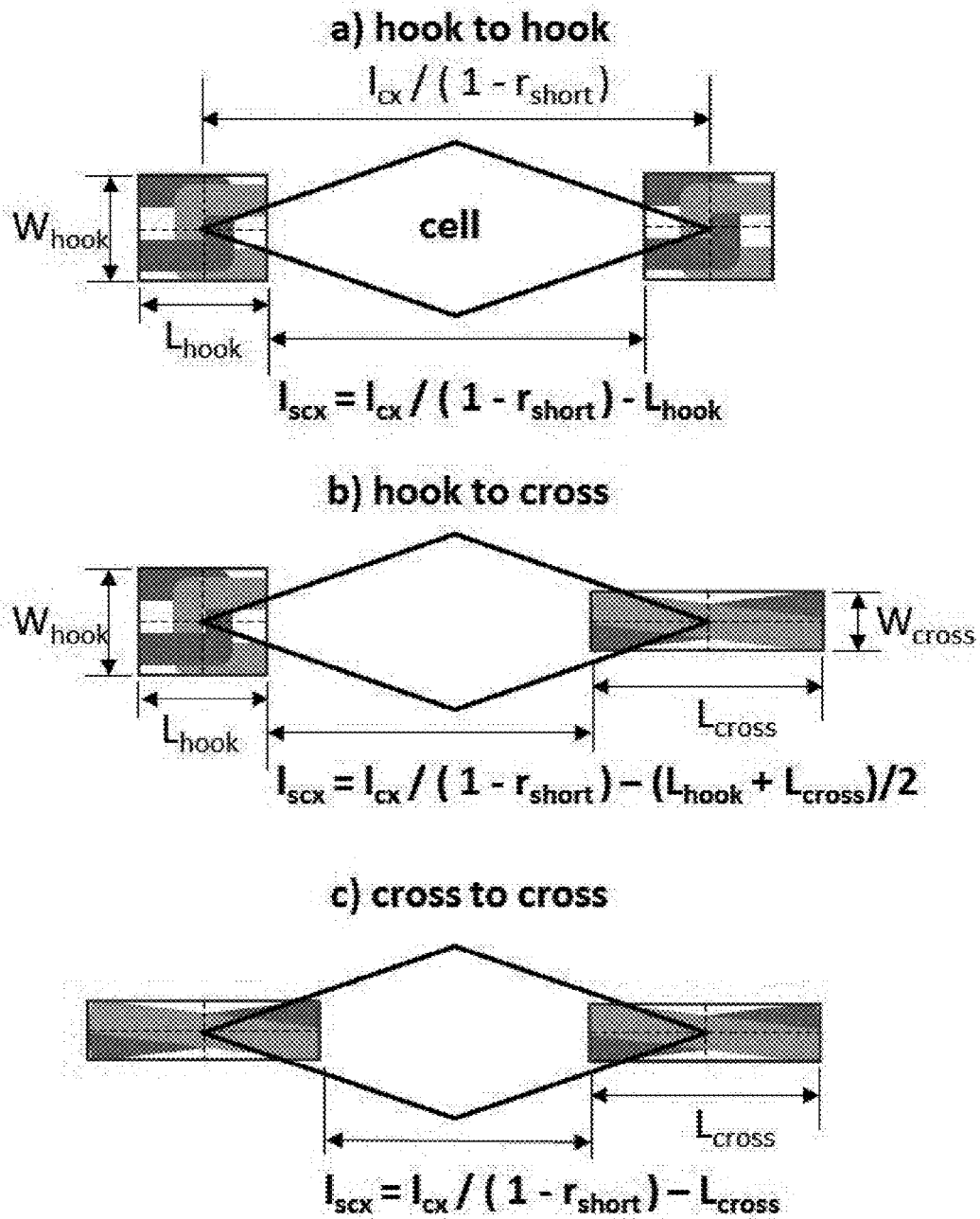
FIG. 27 shows the secure axial length of cell ($l_{scx}$) obtained by applying the nominal length of a plane node model with hooks and crosses of the present invention to each pane of cell in FIG. 26.

$I_{cx}$: Axial length of cell before compression
$I_{cx.load}$: Axial length of cell after compression When the nominal length of the hook and cross plane node model of the present invention (FIG. 40) is applied to the above cell plane, the secure axial length of cell ($I_{scx}$) allowing secure coating without model interference can be obtained (FIG. 27).

The average secure coating volume per node ($V_{sa}$) coated in a cell area employing the secure cell axis length ($I_{scx}$) is as follows:

$$V_{sa} = A_{sa} \times I_{scx}$$

$$I_{scx} = \begin{cases} I_{cx}/(1 - r_{short}) - L_{hook}: & \text{for hook to hook} \\ I_{cx}/(1 - r_{short}) - (L_{hook} + L_{cross})/2: & \text{for hook to cross} \\ I_{cx}/(1 - r_{short}) - L_{cross}: & \text{for cross to cross} \end{cases}$$

Application Example

Depending on the characteristics of a polymer and a drug to be coated when coating is conducted in the secure coating area, the coating-completed (dried) form may be differently shown.

Figure 28:
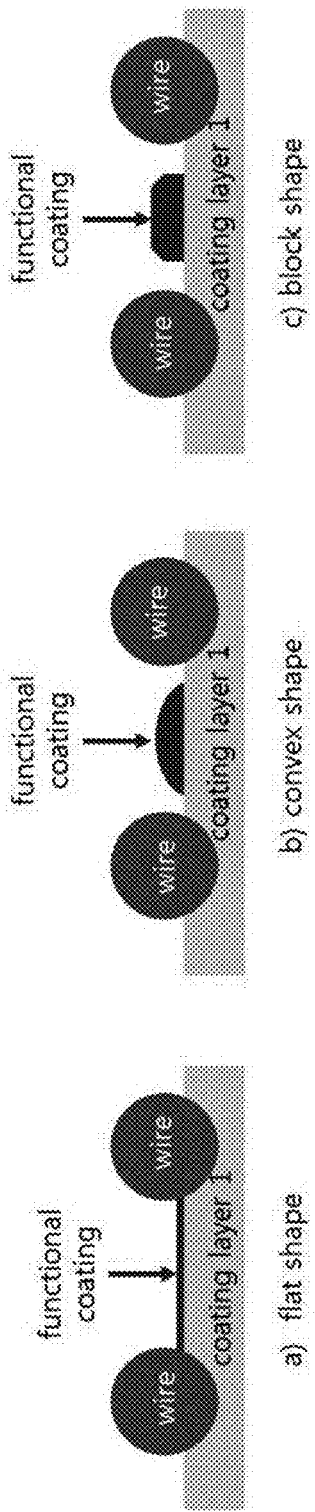
FIG. 28 shows coating-completed (dried) forms varied according to the characteristics of a polymer and a drug coated in a secure coating area.

A coating material exhibiting property, such as low viscosity and hydrophilicity, may have a nearly flat shape after completion of coating (drying); conversely, a coating material exhibiting high viscosity and hydrophobicity may have a slightly convex shape; and a coating material having very high viscosity and hydrophobicity may have a block shape (FIG. 28).

Since the secure coating volume is maintained regardless of the form of coating, the purpose of additional functional coating can be achieved without affecting the loading and deployment in the delivery device.

The entire secure coating area may be used according to the requested purpose, or a particular coating pattern may be formed using a part of the secure coating area.

For example, a pattern of a straight line, a circular line, a spiral line, a point spread line, or the like may be configured.

The coating in the secure coating area does not correspond to a concept of spraying, flowing, or dipping on a part or the entirety of the stent outer wall, which are commonly employed in the prior art, but a concept of targeting and pasting on a particular region, and therefore, a spotting or spot spraying coating method in which quantitative discharge is supported (allowable) is preferable.

The conventional coating method employs an overall wall- or layer-based approach while the outer walls of both the tube stent prepared by a laser cutting process and the wire stent prepared by weaving a wire material have a single layer, from a macroscopic point of view, whereas the present invention is characterized by an individual cell-based approach intensively considering the structure of the stent, the delivery device, and the preparation process, from a microscopic point of view.

The stent may employ various metal materials known in the art as long as the metals are biocompatible or have certain compatibility, and the metal material is preferably a nitinol alloy, stainless steel, tantalum, a tantalum alloy, platinum, a platinum alloy, gold, a gold alloy, a cobalt alloy, a cobalt-chromium alloy, a titanium alloy, and a niobium alloy; more preferably a nitinol alloy, stainless steel, or a cobalt-chromium alloy; most preferably, a nitinol alloy or stainless steel.

The functional material includes biodegradable and non-biodegradable polymers known in the art, and is preferably selected from the group consisting of biodegradable and non-biodegradable polymers, such as gelatin, polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polyurethane (PUR), polydimethylsiloxane (PDMS), silicone (SIL), polyethylene terephthalate (PETP), polytetrafluoroethylene (PTFE), and expanded polytetrafluoroethylene (ePTFE).

The functional material may further a material for an antithrombotic agent, and the material for an antithrombotic agent may employ various known resins alone or in a mixture. For example, polydimethylsiloane (PDMS), polyurethane (PUR), polyeterafluoroethylene (PTFE), or expanded polyterafluoroethylene (ePTFE) may be preferably used.

In addition, the functional material may further include a radiation marker in order to confirm the insertion procedure and insertion state of the wire stent of the present invention through radiography, such as X-ray, CT, or MRI.

The radiation marker may include various radiation markers used in radiography, and the radiation marker is selected from the group consisting of gold (Au), platinum (Pt), silver (Ag), titanium (Ti), tantalum (Ti), niobium (Nb), molybdenum (Mo), rhodium (Rh), palladium (Pd), hafnium (Hf), tungsten (W), iridium (Ir), platinum-iridium (Pt—Ir), barium (Ba), barium sulfate ($BaSO_4$), cobalt (Co), and a mixture thereof. Also, the type of the radiation marker is various, such as a thin film, a rod, and a particle, and the size thereof may be freely used within a range which can be applied in a secure coating area proposed by the present invention.

The functional material may further include an anticancer agent, and preferably, the anticancer agent Still more preferably, the anticancer agent may be selected from the group consisting of cisplatin, carboplatin, oxalyplatin, procarbazine, mechlorethamine, cyclophosphamide, ifosfamide, melphalan, chlorambucil, bisulfan, nitrosourea, camptothecin, irinotecan, dactinomycin, carmustine, rapamycin, daunorubicin, doxorubicin, doxorubicin HCl, idarubicin HCl, bleomycin, plicomycin, mitomycin-C, etoposide, tamoxifen, paclitaxel, docetaxel, transplatinum, 5-fluorouracil, adriamycin, acvicin, aclarubicin, acodazole, ormaplatin, vincristin, vincristin sulfate, vinblastin, vinblastin sulfate, cytarabine, methotrexate, gemcitabine, gemcitabine HCl, capecitabine, and a mixture thereof.

The antiinflammatory agent that may be further included in the functional material may be selected from the group consisting of aspirin, diclofenac, indomethacin, sulindac, ketoprofen, flurbiprofen, iborprofen, naproxen, piroxicam, tenoxicam, tolmetin, ketorolac, oxaprosin, mefenamic acid, fenprofen, nambumetone (Relafen), acetaminophen (Tylenol), and a mixture thereof.

In addition, the functional material may further include an antithrombotic agent, and the antithrombotic agent is selected from the group consisting of aspirin, clopidogrel, indobufen, cilostazol, ticlopidine, beraprost, heparin, and a mixture thereof.

Applications of Secure Coating Area (Radiopaque Application)

Figure 29:
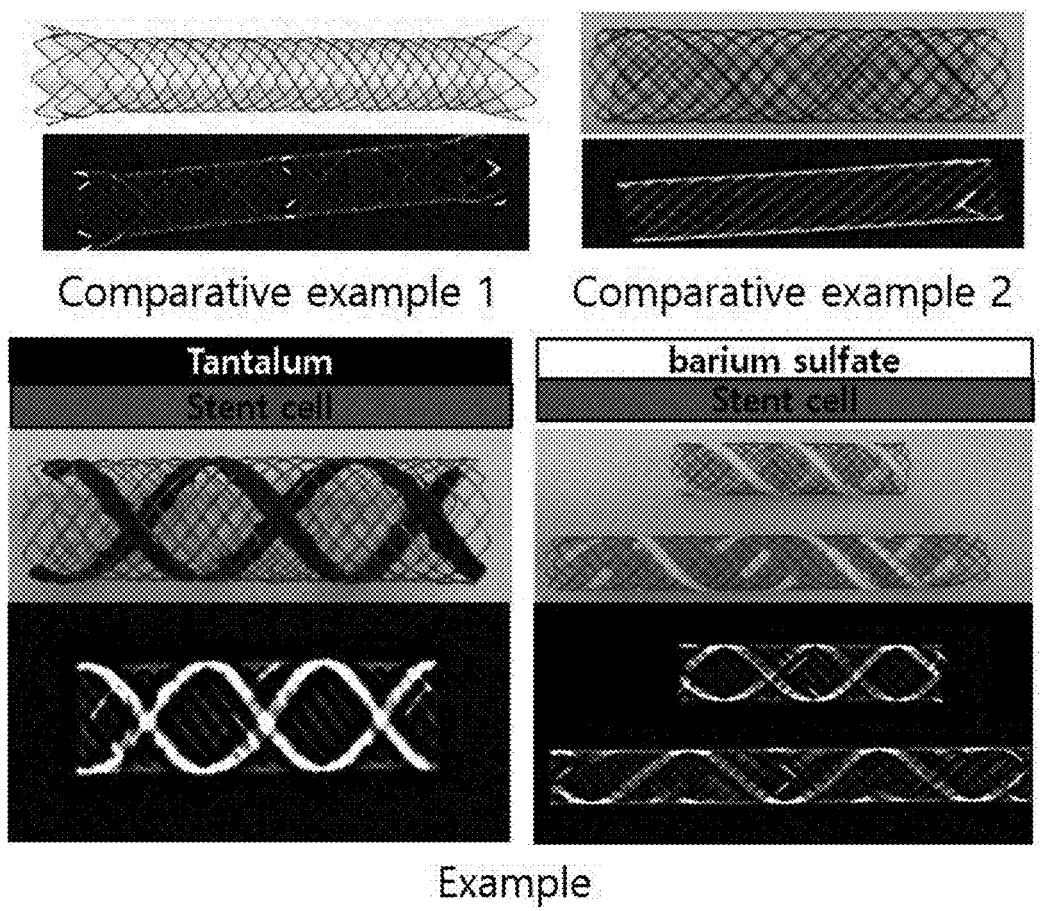
FIG. 29 shows a radiopaque effect confirmed by coating tantalum mixed with a polymer in a secure coating area of the present invention.
Figure 30:
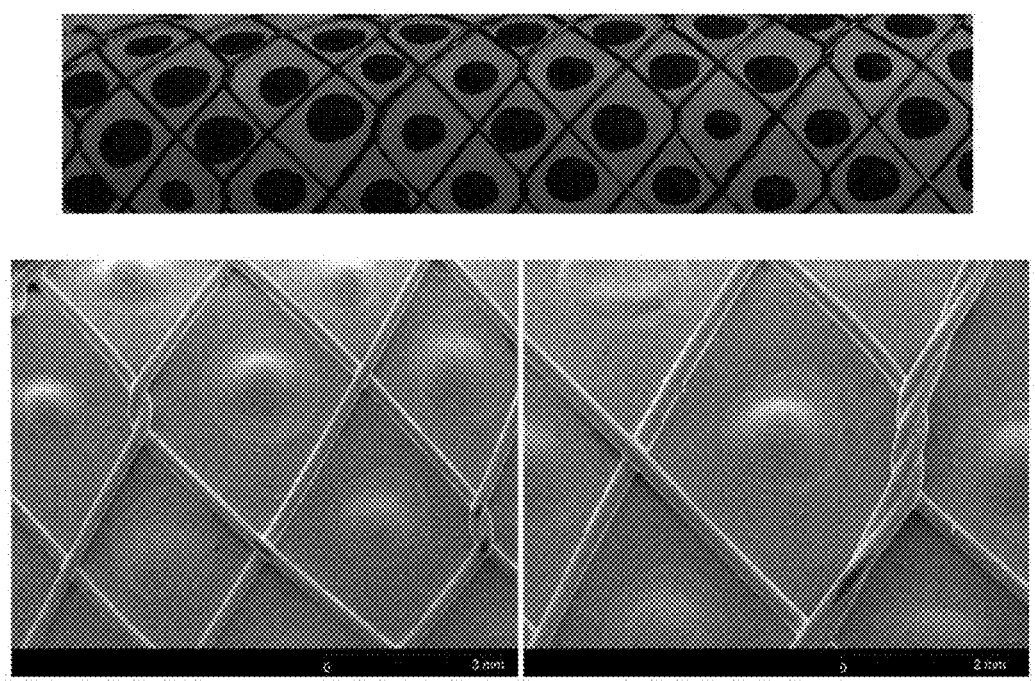
FIGS. 30 to 32 show a stent having secure coating areas coated with tantalum.
Figure 31:
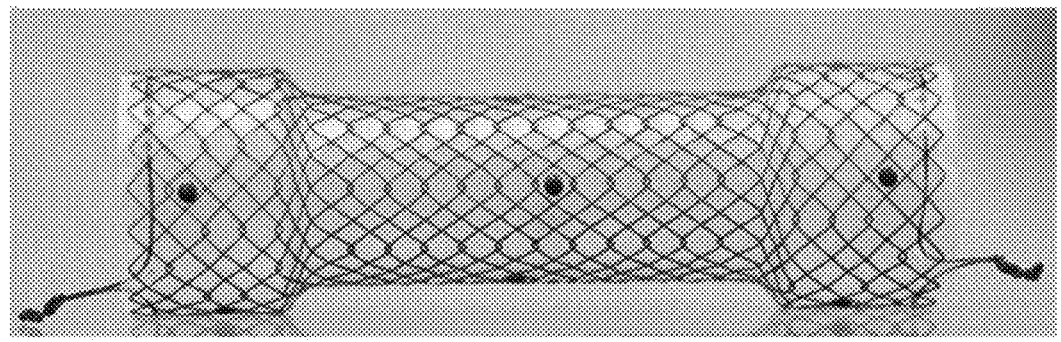
Figure 32:
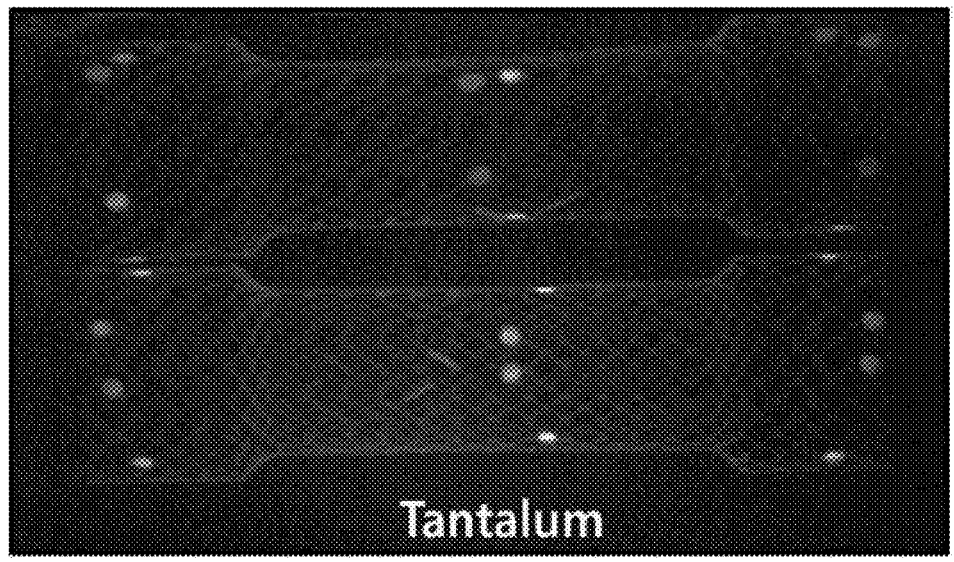
Figure 33:
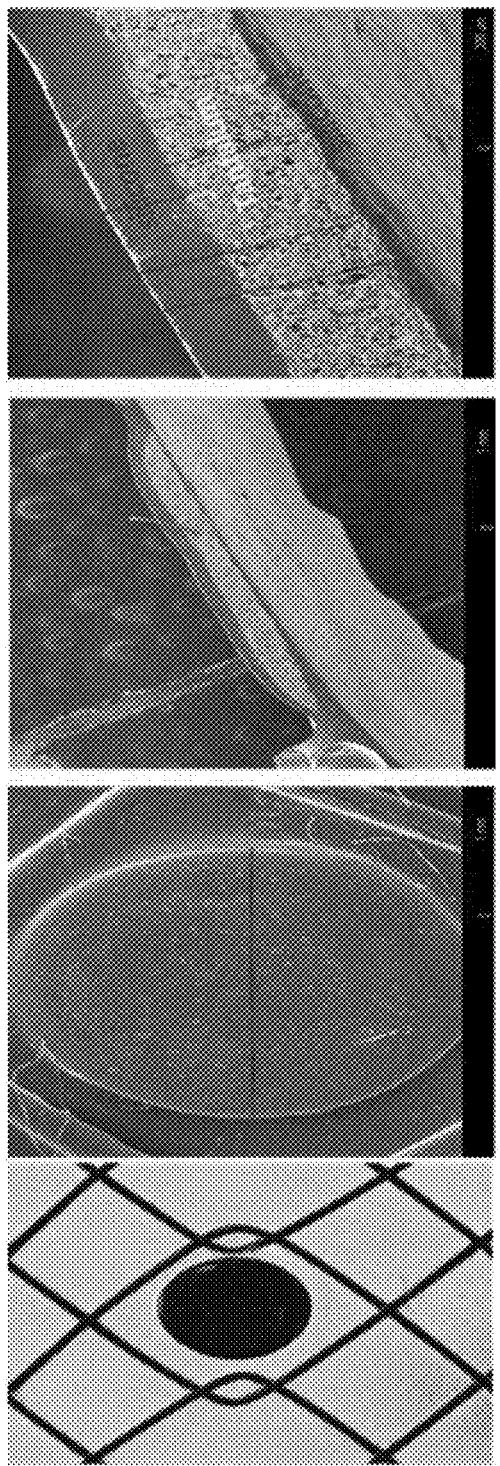
FIG. 33 shows an example in which a multi-layer with tantalum between upper and lower silicon layers is coated in a secure coating area.
Figure 34:
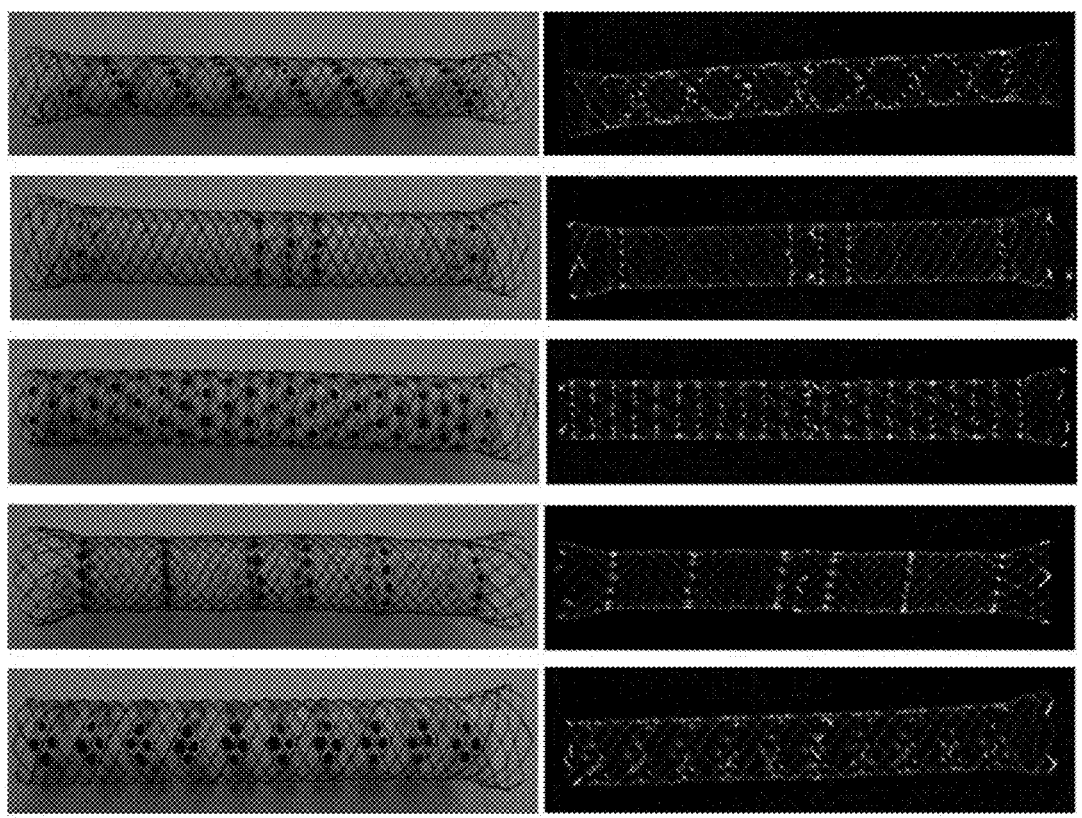
FIGS. 34 to 36 show examples of a radiopaque pattern.
Figure 35:
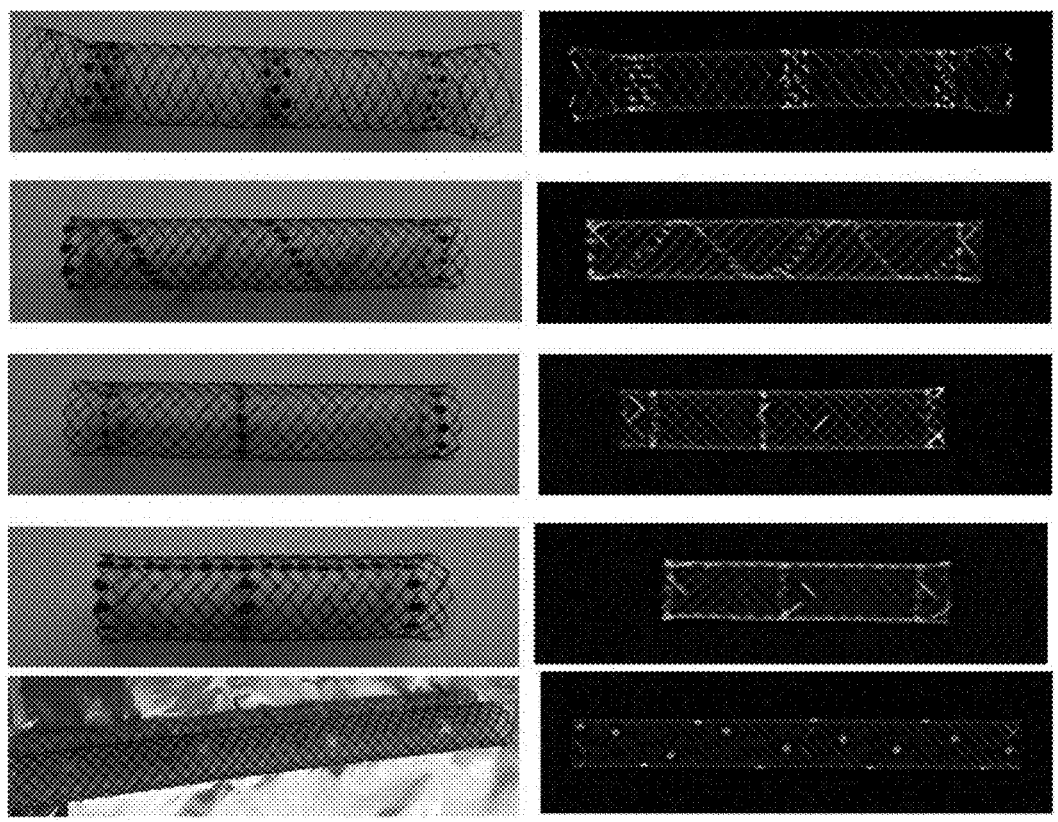
Figure 36:
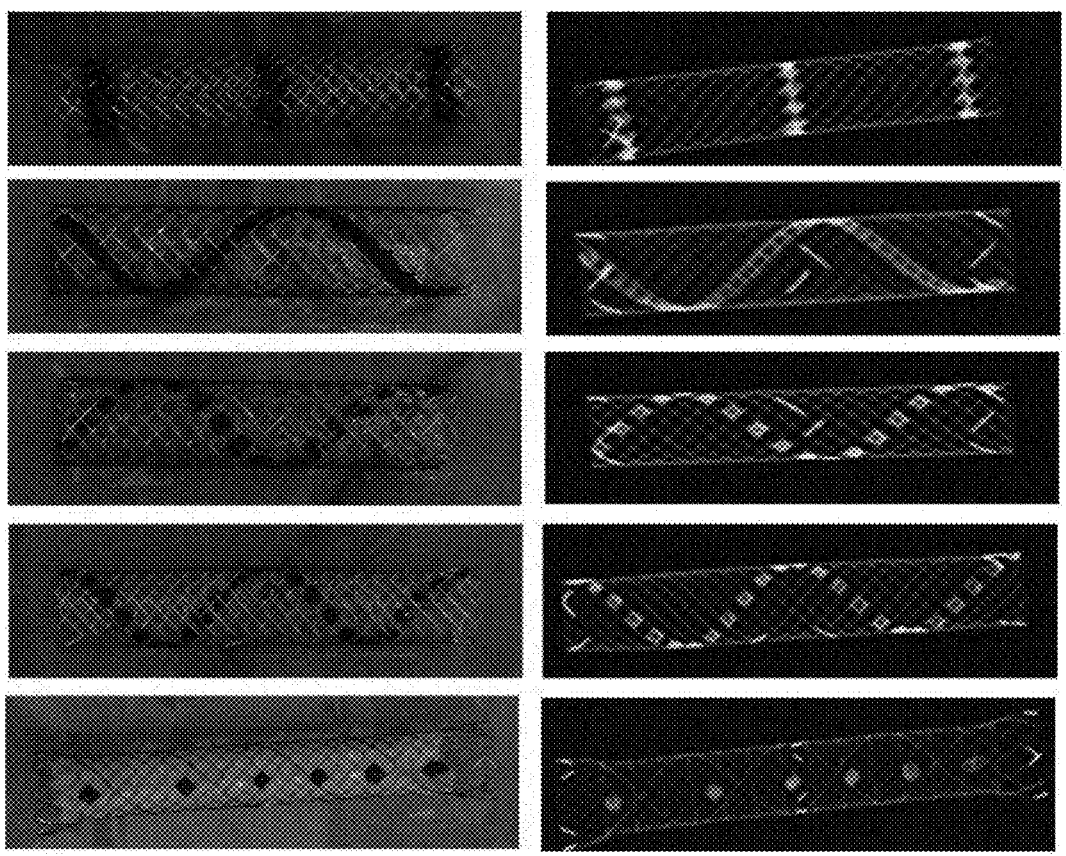

Conventionally, a precious metal, such as gold (Au), platinum (Pt), and platinum-iridium (Pt—Ir), was widely wound on a ring, tube, or stent made of a wire, directly used as a wire material, or vapor-deposited on a metal surface of the stent, thereby ensuring radiopacity characteristics, but according to the present invention, the coating of tantalum mixed with the polymer in the secure coating area is conducted, leading to no additional volume increase even when the stent is compressed and loaded in the delivery device, causing no interference with the loading and deployment of the stent, thereby confirming a more excellent radiopacity effect than the conventional method (FIG. 29). FIGS. 30 to 32 show a stent having secure coating areas coated with tantalum. FIGS. 34 to 36 show examples of the radiopaque pattern.

Applications of Secure Coating Area (Drug Coating Application)

Figure 37:
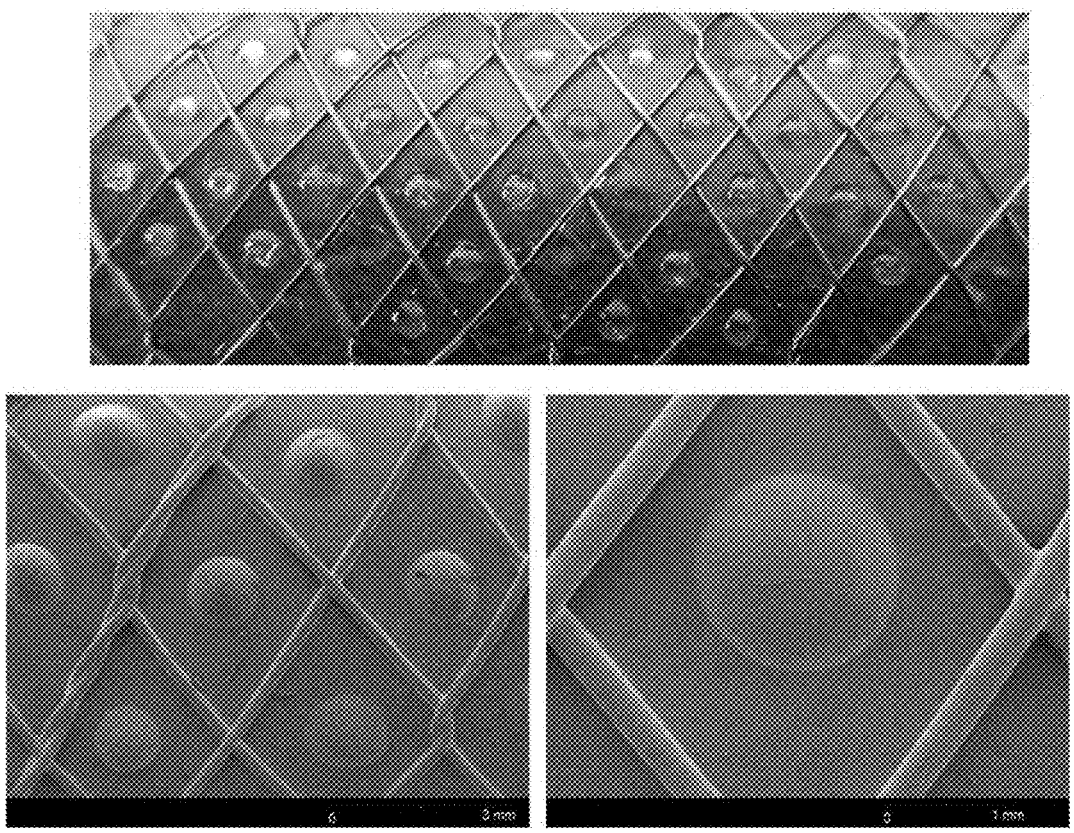
FIG. 37 shows a stent containing paclitaxel, as an anti-cancer drug, coated in secure coating areas.
Figure 38:
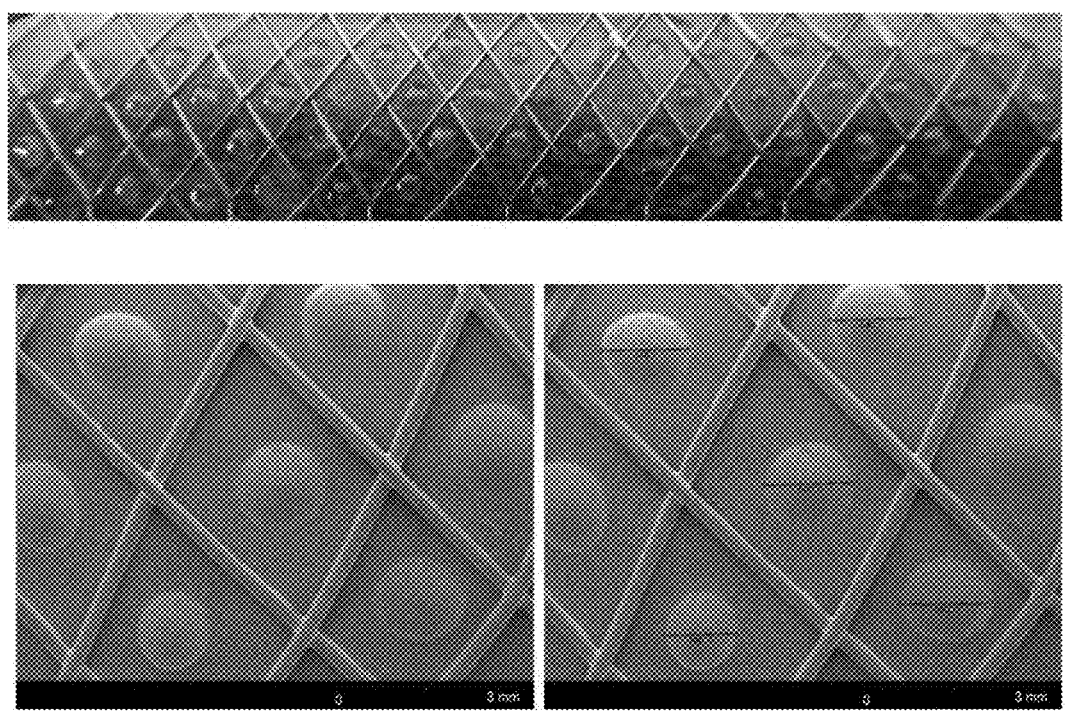
FIG. 38 shows a stent containing gemcitabine, as an anticancer drug, coated in secure coating areas.
Figure 39:
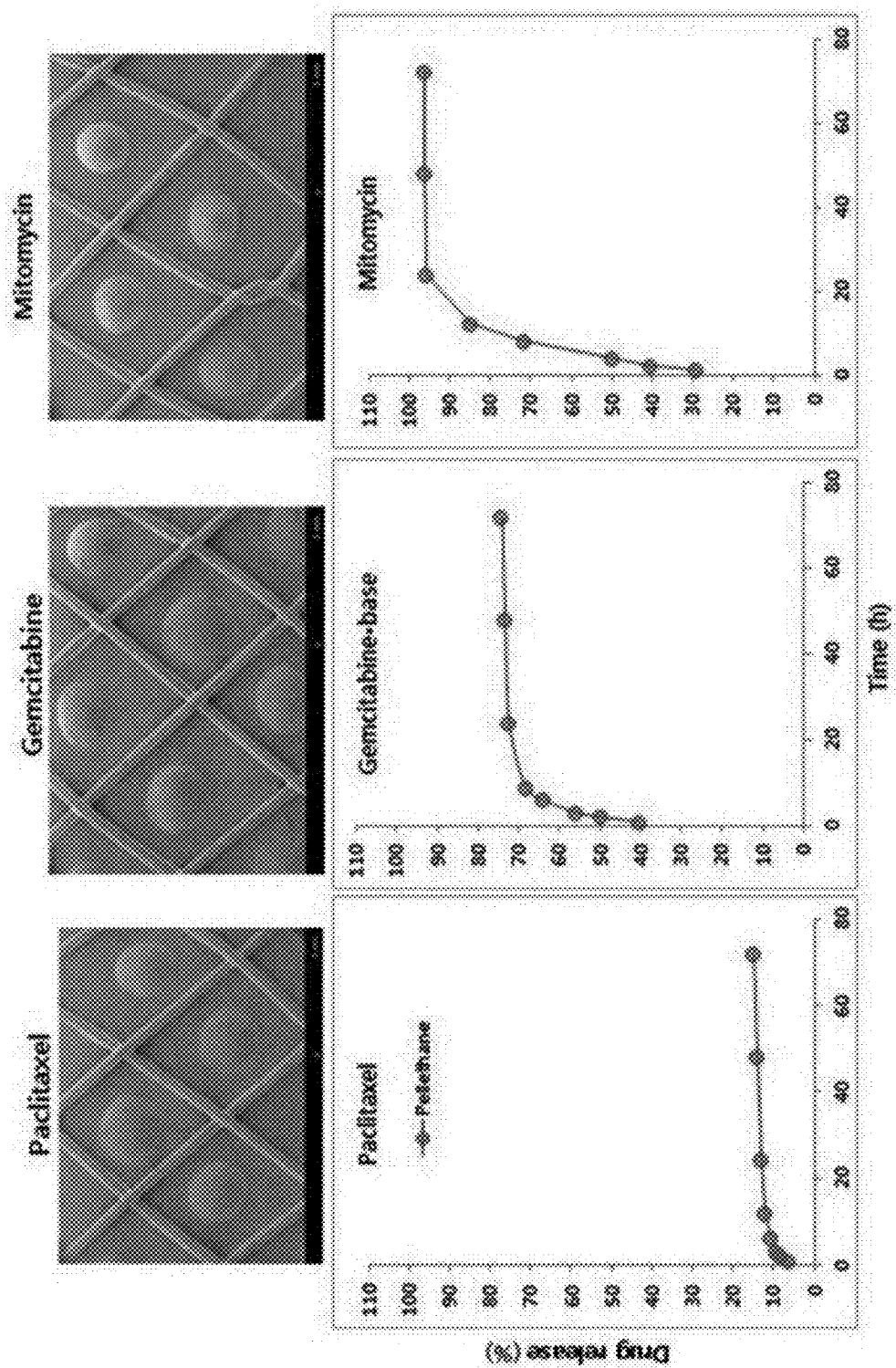
FIG. 39 shows stents containing paclitaxel, gemcitabine, and mitomycin in secure coating areas thereof, respectively, and release profiles of the respective drugs.

The anticancer drugs paclitaxel (FIG. 37), gemcitabine (FIG. 38), and mitomycin were also coated in the secure coating areas in the present invention, and the respective drug release profiles thereof were confirmed (FIG. 39).

In particular, the amount of loading is important for functional drugs, such as anticancer drugs, applied to non-vascular stents, and the application of the cell area-based secure coating area of the present invention enables a stable loading of a large amount of functional drugs.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A stent having a cell area coated with a functional material wherein the cell area has a volume defined by equation 1 below:

$$V_{sa} = A_{sa} \times I_{scx} \qquad \text{Equation 1}$$

wherein in equation 1, $V_{sa}$ represents the average coating volume per node and $A_{sa}$ represents the average coating area per node, the node meaning a hook or cross; and $I_{scx}$ represents the axial length of cell.

2. The stent of claim 1, wherein the stent is a wire stent having a cell area comprising a hook, a cross, or a hook and a cross.

3. The stent of claim 1, wherein the axial length of cell ($I_{scx}$) is defined by equation 2:

$$I_{scx} = \begin{cases} I_{cx}/(1-r_{short}) - L_{hook} : & I_{scx} \text{ is between hook and hook} \\ I_{cx}/(1-r_{short}) - \\ (L_{hook} + L_{cross})/2 : & I_{scx} \text{ is between hook and cross} \\ I_{cx}/(1-r_{short}) - L_{cross} : & I_{scx} \text{ is between cross and cross} \end{cases} \qquad \text{Equation 2}$$

wherein in equation 2, $I_{cx}$ represents the axial length of cell, $r_{short}$ represents the shortening ratio and is defined by equation 3 below, $L_{hook}$ represents the length of hook node and is defined by equation 4 below, and $L_{cross}$ represents the length of hook node and is defined by equation 5 below; wherein in equation 3 below, $L_{stent.load}$ represents the length of stent when the stent is loaded in a delivery device, $L_{stent}$ represents the length of stent before the stent is loaded in the delivery device, and the $r_{short}$ has a value of 0.2-0.6; wherein in equations 4 and 5 below, $\phi_w$ represents the diameter of a wire; wherein in equation 4 below, $SF_{lh}$ represents the length scale factor of hook node and has a value of 4; and wherein in equation 5 below, $SF_{lc}$ represents the length scale factor of cross node and has a value of 5:

$$r_{short} = (L_{stent.load} - L_{stent})/L_{stent.load} \qquad \text{Equation 3}$$

$$L_{hook} = \phi_w \times SF_{lh} \qquad \text{Equation 4}$$

$$L_{cross} = \phi_w \times SF_{lc}. \qquad \text{Equation 5}$$

4. The stent of claim 1, wherein the average coating area per node ($A_{sa}$) is defined by equation 6 below; and wherein in equation 6, $A_{sx}$ represents the maximum coating area and is defined by equation 7 below, and $N_t$ represents the total number of nodes per section of stent and is defined by equation 8 below:

$$A_{sa} = A_{sx}/N_t \qquad \text{Equation 6}$$

$$A_{sx} = \pi(R^2_{ob} - R^2_{ib}) - A_{nd} \qquad \text{Equation 7}$$

$$N_t = N_h + N_c \qquad \text{Equation 8}$$

wherein in equation 7 above, $R_{ob}$ represents the radius of outmost boundary, $R_{ib}$ represents the radius of inmost boundary, and $A_{nd}$ represents the node area per section of stent; and wherein in equation 8 above, $N_h$ represents the number of hook nodes per section of stent, and $N_c$ represents the number of cross nodes per section of stent.

5. The stent of claim 4, wherein the radius of outmost boundary ($R_{ob}$) is defined by equation 9; the radius of inmost boundary ($R_{ib}$) is defined by equation 10; and $A_{nd}$ is defined by equation 11:

$$R_{ob} = \frac{R_{tb}}{\cos(180/N_x)} \qquad \text{Equation 9}$$

$$R_{ib} = \frac{W_{avg}}{2 \cdot \tan(180/N_t)} \qquad \text{Equation 10}$$

$$A_{nd} = (W_{hook} \times H_{hook} \times N_h) + (W_{cross} \times H_{cross} \times N_c) \qquad \text{Equation 11}$$

wherein in equation 9 above, $R_{tb}$ represents the inradius of outmost boundary, and $N_x$ represents the number of virtual hook nodes tangential on the outmost boundary; wherein in equation 10 above, $W_{avg}$ represents the average width of node per section of stent, equation 10 above satisfying conditions of $\pi/(N_t \tan(180/N_t)) \leq 1$; and wherein in equation 11 above, $W_{hook}$ represents the width of hook node, $H_{hook}$ represents the height of hook node, $W_{cross}$ represents the width of cross node, and $H_{cross}$ represents the height of cross node.

6. The stent of claim 5, wherein the average width of node per section of stent ($W_{avg}$) is defined by equation 12 below; the number of virtual hook nodes tangential on the outmost boundary ($N_x$) is defined by equation 13 below; the height of hook node ($H_{hook}$) is defined by equation 14 below; and the height of cross node ($H_{cross}$) is defined by equation 15 below:

$$W_{avg} = W_{total}/N_t \qquad \text{Equation 12}$$

$$N_x = \left\| \frac{180}{\tan^{-1}(W_{avg}/(2R_{tb}))} \right\| \qquad \text{Equation 13}$$

$$H_{hook} = \Phi_w \times SF_{hh} \qquad \text{Equation 14}$$

$$H_{cross} = \Phi_w \times SF_{hc} \qquad \text{Equation 15}$$

wherein in equation 12 above, $W_{total}$ represents the sum total of width of all nodes per section of stent; wherein in equation 13 above, $R_{tb}$ represents the inradius of outmost boundary; wherein in equations 14 and 15 above, $\phi_w$ represents the diameter of wire; wherein in equation 14 above, $SF_{hh}$ represents the height scale factor of hook node and has a value of 3; and wherein in equation 15 above, $SF_{hc}$ represents the length scale factor of cross node and has a value of 2.

7. The stent of claim 6, wherein the sum total of width of all nodes per section of stent ($W_{total}$) is defined by equation 16 below; and the inradius of outmost boundary ($R_{tb}$) is defined by equation 17 below:

$$W_{total} = (W_{hook} \times N_h + W_{cross} \times N_c) \qquad \text{Equation 16}$$

$$R_{tb} = R_{ib} + H_{hook} \qquad \text{Equation 17}$$

wherein in equation 16 above, $W_{hook}$ represents the width of hook node, and $W_{cross}$ represents the width of cross node.

8. The stent of claim 6, wherein the width of hook node ($W_{hook}$) is defined by equation 18 below; and the width of cross node ($W_{cross}$) is defined by equation 19 below:

$$W_{hook} = \phi_w \times SF_{wh} \qquad \text{Equation 18}$$

$$W_{cross} = \phi_w \times SF_{wc} \qquad \text{Equation 19}$$

wherein in equations 18 and 19 above, $\phi_w$ represents the diameter of wire; wherein in equation 18 above, $SF_{wh}$ represents the width scale factor of hook node and has a value of 3.3; and wherein in equation 19 above, $SF_{wc}$ represents the width scale factor of cross node and has a value of 2.

9. A stent having a cell area coated with a functional material, wherein the cell area has a volume defined by equation 20 below:

$$V = 2R \times (I_{ex} - 2R) \times h \qquad \text{Equation 20}$$

wherein in equation 20 above, R represents the radius of cell axial end, $I_{ex}$ represents the axial length of cell, and h represents the thickness or height of cell, and wherein the stent is a tube stent having a cell area formed by a strut.

10. The stent of claim 1, wherein the stent is formed of a material selected from the group consisting of a nitinol alloy, stainless steel, tantalum, a tantalum alloy, platinum, a platinum alloy, gold, a gold alloy, a cobalt alloy, a cobalt-chromium alloy, a titanium alloy, and a niobium alloy.

11. The stent of claim 1, wherein the functional material includes biodegradable and non-biodegradable polymers.

12. The stent of claim 11, wherein the functional material further includes at least one selected from the group consisting of a radiation marker, an anticancer agent, an anti-inflammatory agent, and an antithrombotic agent.

13. The stent of claim 11, wherein the biodegradable and non-biodegradable polymers are selected from the group consisting of gelatin, polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polyurethane (PUR), polydimethylsiloxane (PDMS), silicone (SIL), polyethylene terephthalate (PETP), polytetrafluoroethylene (PTFE), and expanded polytetrafluoroethylene (ePTFE).

14. The stent of claim 12, wherein the radiation marker is selected from the group consisting of gold (Au), platinum (Pt), silver (Ag), titanium (Ti), tantalum (Ti), niobium (Nb), molybdenum (Mo), rhodium (Rh), palladium (Pd), hafnium (Hf), tungsten (W), iridium (Ir), platinum-iridium (Pt—Ir), barium (Ba), barium sulfate (BaSO$_4$), cobalt (Co), and a mixture thereof.

15. The stent of claim 12, wherein the anticancer agent is selected from the group consisting of cisplatin, carboplatin, oxalyplatin, procarbazine, mechlorethamine, cyclophosphamide, ifosfamide, melphalan, chlorambucil, bisulfan, nitrosourea, camptothecin, irinotecan, dactinomycin, carmustine, rapamycin, daunorubicin, doxorubicin, doxorubicin HCl, idarubicin HCl, bleomycin, plicomycin, mitomycin-C, etoposide, tamoxifen, paclitaxel, docetaxel, transplatinum, 5-fluorouracil, adriamycin, acvicin, aclarubicin, acodazole, ormaplatin, vincristin, vincristin sulfate, vinblastin, vinblastin sulfate, cytarabine, methotrexate, gemcitabine, gemcitabine HCl, capecitabine, and a mixture thereof.

16. The stent of claim 12, wherein the antiinflammatory agent is selected from the group consisting of aspirin, diclofenac, indomethacin, sulindac, ketoprofen, flurbiprofen, iborprofen, naproxen, piroxicam, tenoxicam, tolmetin, ketorolac, oxaprosin, mefenamic acid, fenprofen, nambumetone (Relafen), acetaminophen (Tylenol), and a mixture thereof.

17. The stent of claim 12, wherein the antithrombotic agent is selected from the group consisting of aspirin, clopidogrel, indobufen, cilostazol, ticlopidine, beraprost, heparin, and a mixture thereof.

\* \* \* \* \*